United States Patent
Cockerill et al.

(10) Patent No.: US 6,169,091 B1
(45) Date of Patent: Jan. 2, 2001

(54) BICYCLIC HETEROAROMATIC COMPOUNDS AS PROTEIN TYROSINE KINASE INHIBITORS

(75) Inventors: George Stuart Cockerill; Stephen Barry Guntrip; Stephen Carl McKeown, all of Stevenage; Martin John Page, Abingdon; Kathryn Jane Smith; Sadie Vile, both of Stevenage; Alan Thomas Hudson, Otford; Paul Barraclough, Maidstone; Karl Witold Franzmann, London, all of (GB)

(73) Assignee: Glaxo Wellcome Inc., Research Triangle Park, NC (US)

( * ) Notice: Under 35 U.S.C. 154(b), the term of this patent shall be extended for 0 days.

(21) Appl. No.: 09/051,324

(22) PCT Filed: Oct. 10, 1996

(86) PCT No.: PCT/EP96/04399

§ 371 Date: Aug. 26, 1998

§ 102(e) Date: Aug. 26, 1998

(87) PCT Pub. No.: WO97/13771

PCT Pub. Date: Apr. 17, 1997

(30) Foreign Application Priority Data

Oct. 11, 1995 (GB) .................................................. 9520845
Jul. 13, 1996 (GB) .................................................. 9614757

(51) Int. Cl.[7] ..................... C07D 487/04; A61K 31/4745

(52) U.S. Cl. ........................................... 514/258; 544/279

(58) Field of Search ..................................... 514/258, 301, 514/302, 303; 544/256, 278, 279, 280; 546/113, 114, 115, 122, 123

(56) References Cited

FOREIGN PATENT DOCUMENTS

| 43 08 104 | 9/1994 | (DE) . |
|---|---|---|
| 0 370 704 B1 | 5/1990 | (EP) . |
| 0 414 386 | 2/1991 | (EP) . |
| 0 452 002 A2 | 10/1991 | (EP) . |
| 0534 341 A1 | 3/1993 | (EP) . |
| WO86/06718 | 11/1986 | (WO) . |
| WO 93/13097 * | 7/1993 | (WO) . |
| WO 93/18035 | 9/1993 | (WO) . |
| WO93/17682 | 9/1993 | (WO) . |
| 94 04526 | 3/1994 | (WO) . |
| WO 95/00511 * | 1/1995 | (WO) . |
| 95 19774 | 7/1995 | (WO) . |

OTHER PUBLICATIONS

Bioorganic & Medical Chemistry Letters, vol. 4, No. 1, pp. 173–176, 1994 Zydowsky et al "Synthesis and In vitro Evaluation of Fused Ring Heterocycle–Containing Angiotensin II Antagonists".

Tetrahedron vol. 27, pp 487 to 499 Robba et al "Thienopyrimidines—II Etude De La Thieno [3,2–d]Pyrimidine et de Quelques Derives" (1971).

Cell, vol. 50, 823–829 Hunter "A Thousand and One Protein Kinases", (1987).

* cited by examiner

Primary Examiner—Mukund J. Shah
Assistant Examiner—Deepak R. Rao
(74) Attorney, Agent, or Firm—John L. Lemanowicz

(57) ABSTRACT

Substituted heteroaromatic compounds of formula (A) wherein X is N or CH; in which (a) represents a fused 5, 6 or 7-membered heterocyclic ring and $R^3$ is a group $ZR^4$ wherein Z is joined to $R^4$ through a $(CH_2)p$ group in which p is 0, 1, or 2 and Z represents a group $V(CH_2)$, $V(CF_2)$, $(CH_2)V$, $(CF_2)V$, $V(CRR')$, $V(CHR)$ or V where R and R' are each $C_{1-4}$ alkyl and in which V is a hydrocarbyl group containing 0, 1 or 2 carbon atoms, carbonyl, dicarbonyl, CH(OH), CH(CN), sulphonamide, amide, O, $S(O)_m$ or $NR^b$ where $R^b$ is hydrogen or $R^b$ is $C_{1-4}$ alkyl; and $R^4$ is an optionally substituted $C_{3-6}$ cycloalkyl or an optionally substituted 5, 6, 7, 8, 9 or 10-membered carbocyclic or heterocyclic moiety; or $R^3$ is a group $ZR^4$ in which Z is $NR^b$, and $NR^b$ and $R^4$ together form an optionally substituted 5, 6, 7, 8, 9 or 10-membered carbocyclic or heterocyclic moiety, are protein tyrosine kinase inhibitors. The compounds are described, as are methods for their preparation, pharmaceutical compositions including such compounds and their use in medicine, for example in the treatment of psoriasis, fibrosis, atherosclerosis, restenosis, auto-immune disease, allergy, asthma, transplantation rejection, inflammation, thrombosis, nervous system diseases, and cancer.

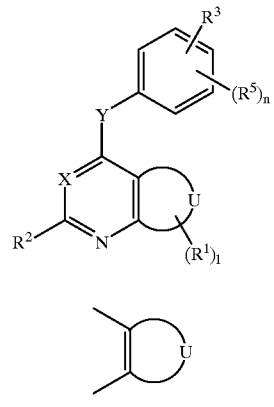

15 Claims, No Drawings

BICYCLIC HETEROAROMATIC COMPOUNDS AS PROTEIN TYROSINE KINASE INHIBITORS

This application is a 371 of PCT/EP96/04399 filed Oct. 10, 1996.

The present invention relates to a series of substituted heteroaromatic compounds, methods for their preparation, pharmaceutical compositions containing them and their use in medicine. In particular, the invention relates to bioisosteres of quinoline and quinazoline derivatives which exhibit protein tyrosine kinase inhibition.

Protein tyrosine kinases catalyse the phosphorylation of specific tyrosyl residues in various proteins involved in the regulation of cell growth and differentiation (A. F. Wilks, Progress in Growth Factor Research, 1990 (2), 97–111). Protein tyrosine kinases can be broadly classified as growth factor receptor (e.g. EGF-R, PDGF-R, FGF-R and c-erbB-2) or non-receptor (e.g. c-src, bcr-abl) kinases. Inappropriate or uncontrolled activation of many of these kinases i.e. aberrant protein tyrosine kinase activity, for example by over-expression or mutation, has been shown to result in uncontrolled cell growth.

Aberrant activity of protein tyrosine kinases such as c-erbB-2, c-src, p56lck, EGF-R, PDGF-R, and zap70 has been implicated in human malignancies.

Aberrant EGF-R activity has, for example, been implicated in cancers of the head and neck, and aberrant c-erbB-2 activity in breast, ovarian, non-small cell lung, pancreatic, gastric and colon cancers. Inhibitors of protein tyrosine kinase should therefore provide a treatment for tumours such as those outlined above.

Aberrant protein tyrosine kinase activity has also been implicated in a variety of other disorders: psoriasis, (Dvir et al, J.Cell.Biol; 1991, 113, 857–865), fibrosis, atherosclerosis, restenosis, (Buchdunger et al, Proc.Natl.Acad.Sci. U.S.A.; 1991, 92 2258–2262), auto-immune disease, allergy, asthma, transplantation rejection (Klausner and Samelson, Cell; 1991, 64 875–878), inflammation (Berkois, Blood; 1992, 79(9), 2446–2454), thrombosis (Salari et al, FEBS; 1990, 263(1), 104–108) and nervous system diseases (Ohmichi et al, Biochemistry, 1992, 31, 4034–4039). Inhibitors of the specific protein tyrosine kinases involved in these diseases eg PDGF-R in restenosis and EGF-R in psoriasis, should lead to novel therapies for such disorders. P561ck and zap 70 are indicated in disease conditions in which T cells are hyperactive eg rheumatoid arthritis, autoimmune disease, allergy, asthma and graft rejection.

WO 9519774 discloses bicyclic derivatives of formula (I):

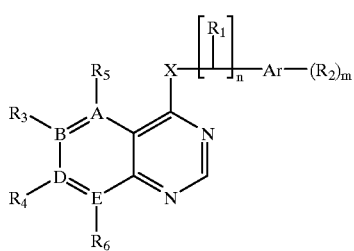

in which A to E are nitrogen or carbon and at least one of A to E is nitrogen; or two adjacent atoms together are N, O or S; $R_1$ is H or alkyl and n is 0, 1 or 2; and $R_2$ includes optionally substituted alkyl, alkoxy, cycloalkoxy, cycloalkoxy, or 2 together form a carbocycle or heterocycle, and m is 0 to 3. The compounds are said to inhibit epidermal growth factor receptor tyrosine kinase and suggested uses include the treatment of cancer, psoriasis, kidney disease, pancreatitis and contraception.

EP0635507 discloses a class of tricyclic quinazoline derivatives of the formula (III):

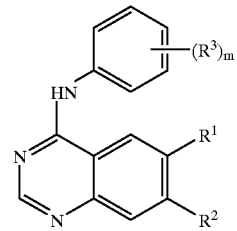

wherein $R^1$ and $R^2$ together form specified optionally substituted groups containing at least one heteroatom so as to form a 5 or 6-membered ring, in which there is a N atom at the 6 position of the quinazoline ring. $R^3$ includes independently hydrogen, hydroxy, halogeno, (1–4C)alkyl, (1–4C)alkoxy di-[(1–4C)alkyl]amino, or (2–4C)alkanoylamino. The above citation notes that receptor tyrosine kinases in general, which are important in the transmission of biochemical signals initiating cell replication, are frequently present in common human cancers such as breast cancer (Sainsbury et al Brit. J. Cancer 1988, 58, 458). This citation also states that tyrosine kinase activity is rarely detected in normal cells whereas it is frequently detectable in malignant cells (Hunter, *Cell,* 1987, 50, 823) and it is suggested that inhibitors of receptor tyrosine kinase should be of value as inhibitors of the growth of mammalian cancer cells (Yaish et al. Science, 1988, 242, 933). This citation therefore has the aim of providing quinazoline derivatives which inhibit receptor tyrosine kinases involved in controlling the tumourigenic phenotype.

The above compounds suffer the disadvantage that they are more difficult to synthesize than their quinoline and quinazoline counterparts on account of the additional structural complexity and accordingly there is a need for quinoline and quinazoline deriatives which are capable of inhibiting protein tyrosine kinase activity and yet are relatively simple to synthesize. There is no reference in the above citation to any such bicyclic heterocyclic system capable of inhibiting protein tyrosine kinase activity and the present invention seeks to fill this omission.

Selective inhibition of the EGF receptor is, however, disclosed by Fry et al (Science, 265, 1093 (1994)). This citation discloses that the compound:

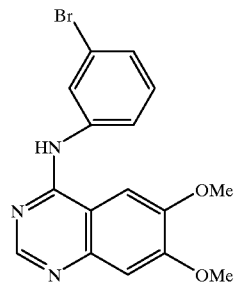

is a highly selective inhibitor of the EGF receptor tyrosine kinase at picomolar concentrations while inhibiting other tyrosine kinases only at micromolar or higher concentrations. This compound does not however exhibit good in vivo activity in contrast to the compounds of the present invention.

WO 93/17682 and Bioorg Med Chem Lett (1993, 4 (1), 173–176) disclose compounds which block angiotensin II receptors and have the general formula (IV)

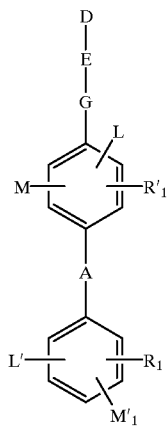

(IV)

in which D is a bicyclic heterocyle comprising a 6-membered ring fused to another 6-membered ring, the bicyclic heterocycle comprising at least one heteroatom selected from N, O and S, and each fused ring independently containing 0 to 3 N atoms, 1 N atom and 1 O atom, 1 N atom or 1 S atom, 1 O atom and 1 S atom, 2 O atoms, 2 S atoms or 1 O atom or 1 S atom, with the remaining ring atoms being carbon atoms. Pendant $R_1$ and $R'_1$ groups include tetrazolyl, N substituted amino, N substituted amide, N substituted urea, carboxylate, amino sulphone, carbonyl, methylene alkoxy, sulphonate and phosphate.

WO 93/18035 and Bioorg Med Chem Lett (1993, 4 (1), 173–176) relate to further angiotension II receptor blocking compounds of formula (I) above, with the difference that D in formula (I) now represents a bicyclic heterocycle comprising a 6-membered ring fused to a 5-membered ring, the bicyclic heterocycle comprising at least one heteroatom selected from N, O and S. In this application, the 6-membered ring comprises 0 to 3 N atoms, 1 N atom and 1 O atom, 1 N atom and 1 S atom, 1 O atom and 1 S atom, 2 O atoms, 2 S atoms, 1 O atom, or 1 S atom; and the 5-membered ring comprises 0 to 3 N atoms, 1 N atom and 1 O atom, 1 N atom and 1 S atom, 1 O atom and 1 S atom, 1 O atom, or 1 S atom with the remaining atoms in the fused rings being carbon atoms.

WO 86/06718 relates to a class of mono- and di- Mannich bases, derived from 4-(7'-substituted-1',5'-naphthyridin-4'-ylamino)phenols and 4-(7'-substituted-quinolin-4'-ylamino)-phenols of formula (V):

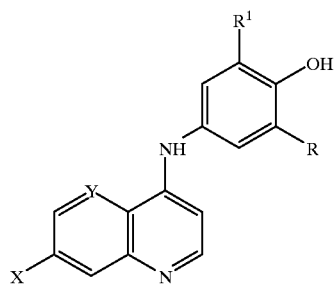

(V)

in which Y is N or CH, and $R^1$ and $R^2$ are independently hydrogen or specified substituted amino groups. The compounds of formula (II) exhibit antimalarial activity.

EP 0534341 relates to the preparation of 4-[(ar)alkoxy] pyrimidines for use as pesticides and agrochemical fungicides. This application discloses compounds of formula (VI):

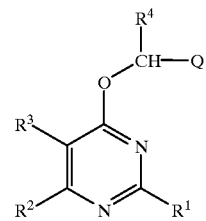

(VI)

in which $R^2$ and $R^3$ together form an unsaturated 5-membered ring, together with the C atoms to which they are attached, containing an O or S atom; or $R^2$ and $R^3$ together form a saturated 5, 6 or 7-membered ring which may contain an O or S atom.

EP 0452002 relates to 4-substituted thieno [2,3-d], [3,2-d] and [3,4-d] pyrimidines of formula (VII) below having fungicidal, insecticidal and miticidal utility:

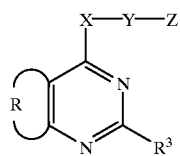

(VII)

in which

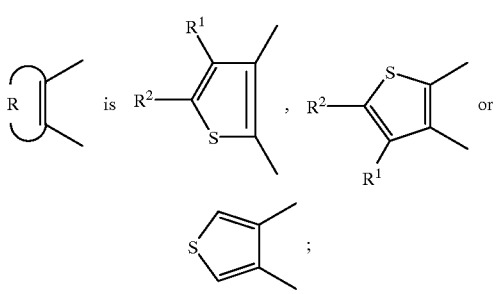

and X includes O, S or $NR^4$ where $R^4$=H or $C_{1-4}$ alkyl; Y includes a carbocyclic ring which may contain a heteroatom; and Z is a $C_{3-8}$ cycloalky or phenyl.

Tetrahedron (1971, 27 487–499) concerns an academic study which discloses nucleophilic substitution reactions of 4-chlorothieno[3,2-d]pyrimidines to produce a number of compounds in which the 4-substituent is bound to the pyrimidine via a heteroatom, for example 4-phenoxythieno [3,2-d]pyrimidine is exemplified.

EP 0370704 relates to the preparation of 4-(benzylamino) pyrimidines of formula (VIII) as pesticides:

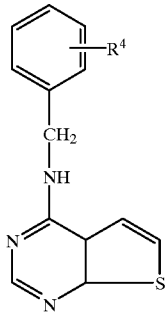

(VIII)

It is a general object of the present invention to provide compounds suitable for the treatment of disorders mediated by protein tyrosine kinase activity, and in particular treatment of the above mentioned disorders.

In addition to the treatment of tumours, the present invention envisages that other disorders mediated by protein tyrosine kinase activity may be treated effectively by preferential inhibition of the appropriate protein tyrosine kinase activity.

Broad spectrum inhibition of protein tyrosine kinase may not provide optimal treatment of, for example tumours, and could in certain cases even be deterimental to subjects since protein tyrosine kinases provide an essential role in the normal regulation of cell growth.

It is another object of the present invention to provide compounds which preferentially inhibit protein tyrosine kinases, such as c-erbB-2, p561ck, EGF-R and PDGF-R protein tyrosine kinases.

A further object of the present invention is to provide compounds useful in the treatment of protein tyrosine kinase related diseases which minimise undesirable side-effects in the recipient.

The present invention relates to heterocyclic compounds which may be used to treat disorders mediated by protein tyrosine kinases and in particular have anti-cancer properties. More particularly, the compounds of the present invention are potent inhibitors of protein tyrosine kinases such as c-erbB-2, EGF-R and p561ck thereby allowing clinical management of particular diseased tissues.

The present invention envisages, in particular, the treatment of human malignancies, for example breast, stomach, ovary, colon, lung and pancreatic tumours, especially those driven by c-erbB-2, using the compounds of the present invention. For example, the invention includes compounds which are highly active against the c-erbB-2 protein tyrosine kinase in preference to the EGF receptor kinase hence allowing treatment of c-erbB-2 driven tumours.

More particularly, the present invention envisages that disorders mediated by protein tyrosine kinase activity may be treated effectively by inhibition of the appropriate protein tyrosine kinase activity in a relatively selective manner, thereby minimising potential side effects.

Accordingly, the present invention provides a compound of formula (A):

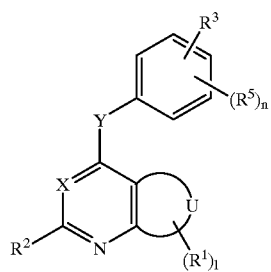

(A)

or a pharmaceutically acceptable salt thereof,
wherein X is N or CH;
wherein

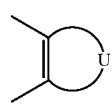

represents a fused 5, 6 or 7-membered heterocyclic ring containing 1 to 5 heteroatoms which may be the same or different and which are selected from N, O or $S(O)_m$, wherein m is 0, 1 or 2, the heterocyclic ring containing a total of 1, 2 or 3 double bonds inclusive of the bond in the pyridine or pyrimidine ring, with the provisos that the heterocyclic ring does not form part of a purine and that the fused heterocyclic ring does not contain two adjacent O or $S(O)_m$ atoms;

Y is a group $W(CH_2)$, $(CH_2)W$, or W, in which W is O, $S(O)_m$, or $NR^a$ wherein m is as defined above and $R^a$ is hydrogen or a $C_{1-8}$ alkyl group;

each $R^1$ independently represents a 5- or 6-membered heterocyclic ring containing 1 to 4 heteroatoms selected from N, O or $S(O)_m$, wherein m is as defined above, with the proviso that the ring does not contain two adjacent O or $S(O)_m$ atoms, optionally substituted by one or more groups independently selected from hydroxy, halogen, trifluoromethyl, trifluoromethoxy, nitro, amino, cyano, $C_{1-4}$ alkyl, $C_{1-4}$ alkoxy, $C_{1-4}$ alkylthio, $C_{1-4}$ alkyl carbonyl, formyl, carboxy, $C_{1-4}$ alkoxy carbonyl, carboxamide, $C_{1-4}$ alkylamino carbonyl, $(C_{1-4}$ alkyl)amino, di-$(C_{1-4}$ alkyl)amino; or each $R^1$ is independently selected from the group comprising amino, hydrogen, halogen, hydroxy, nitro, formyl, carboxy, trifluoromethyl, trifluoromethoxy, carbamoyl, ureido, $C_{1-8}$ alkyl, $C_{1-8}$ alkoxy, $C_{3-8}$ cycloalkoxyl, $C_{4-8}$ alkylcycloalkoxy, $C_{1-8}$ alkoxycarbonyl, N-$C_{1-4}$ alkylcarbamoyl, N,N-di-[$C_{1-4}$ alkyl]carbamoyl, hydroxyamino, $C_{1-4}$ alkoxyamino, $C_{2-4}$ alkanoyloxyamino, $C_{1-4}$ alkylamino, di[$C_{1-4}$ alkyl] amino, pyrrolidin-1-yl, piperidino, morpholino, thiomorpholino, thiomorpholino-1,1-dioxide, piperazin-1-yl, 4-$C_{1-4}$ alkylpiperazin-1-yl, $C_{1-8}$ alkylthio, arylthio, $C_{1-4}$ alkylsulphinyl, arylsulphinyl, $C_{1-4}$ alkylsulphonyl, arylsulphonyl, halogeno-$C_{1-4}$ alkyl, hydroxy-$C_{1-4}$ alkyl, $C_{2-4}$ alkanoyloxy-$C_{1-4}$ alkyl, $C_{1-4}$ alkoxy-$C_{1-4}$ alkyl, carboxy-$C_{1-4}$ alkyl, $C_{1-4}$ alkoxycarbonyl-$C_{1-4}$-alkyl, amino-$C_{1-4}$ alkyl, $C_{1-4}$ alkylamino-$C_{1-4}$ alkyl, di-[$C_{1-4}$ alkyl]amino-$C_{1-4}$ alkyl, [di-$C_{1-4}$ alkyl]amino-$C_{1-4}$ alkylene-($C_{1-4}$ alkyl)amino, $C_{1-4}$alkylamino-$C_{1-4}$alkylene-($C_{1-4}$alkyl)amino, hydroxy-$C_{1-4}$alkylene-($C_{1-4}$alkyl)amino, piperidino-$C_{1-4}$alkyl, morpholino-$C_{1-4}$ alkyl, thiomorpholino-$C_{1-4}$ alkyl, thiomorpholino-1,1-dioxide-$C_{1-4}$ alkyl, piperazin-1-yl-$C_{1-4}$ alkyl, $C_{1-4}$ alkylthio-$C_{1-4}$ alkyl, phenoxy-$C_{1-4}$ alkyl, anilino-$C_{1-4}$ alkyl, phenylthio-$C_{1-4}$ alkyl, cyano-$C_{1-4}$ alkyl, halogeno-$C_{2-4}$ alkoxy, hydroxy-$C_{2-4}$ alkoxy, $C_{2-4}$ alkanoyloxy-$C_{2-4}$ alkoxy, $C_{1-4}$ alkoxy-$C_{2-4}$ alkoxy, carbamoyl-$C_{1-4}$ alkoxy, amino-$C_{2-4}$ alkoxy, $C_{1-4}$ alkylamino-$C_{2-4}$ alkoxy, di-[$C_{1-4}$ alkyl]amino-$C_{2-4}$ alkoxy, phenyl-$C_{1-4}$ alkoxy, phenoxy-$C_{2-4}$ alkoxy, anilino-$C_{2-4}$ alkoxy, phenylthio-$C_{2-4}$ alkoxy, piperidino-$C_{2-4}$ alkoxy, morpholino-$C_{2-4}$ alkoxy, thiomorpholino-$C_{2-4}$ alkoxy, thiomorpholino-1,1-dioxide-$C_{2-4}$ alkoxy, piperazin-1-yl-$C_{2-4}$ alkoxy, halogeno-$C_{2-4}$ alkylamino, hydroxy-$C_{2-4}$ alkylamino, $C_{2-4}$ alkanoyloxy-$C_{2-4}$ alkylamino, $C_{1-4}$ alkoxy-$C_{2-4}$ alkylamino, phenyl-$C_{1-4}$ alkylamino, phenoxy-$C_{2-4}$ alkylamino, anilino-$C_{2-4}$ alkylamino, phenylthio-$C_{2-4}$ alkylamino, $C_{2-4}$ alkanoylamino, $C_{1-4}$ alkoxycarbonylamino, $C_{1-4}$ alkylsulphonylamino, benzamido, benzenesulphonamido, 3-phenylureido, 2-oxopyrrolidin-1-yl, 2,5-dioxopyrrolidin-1-yl, halogeno-$C_{2-4}$ alkanoylamino, hydroxy-$C_{2-4}$ alkanoylamino, $C_{1-4}$ alkoxy-$C_{2-4}$ alkanoylamino, and carboxy-$C_{2-4}$ alkanoylamino, and wherein said benzamido or benzenesulphonamido substitutent or any anilino, phenoxy or phenyl group on a $R^1$ substituent may optionally bear one or two halogeno, $C_{1-4}$ alkyl or $C_{1-4}$ alkoxy substituents;

and l is 0 to 3;

or when l is 2 or 3, two adjacent $R^1$ groups together form an optionally substituted methylenedioxy or ethylenedioxy group;

$R^2$ is selected from the group comprising; hydrogen, halogen, trifluoromethyl, $C_{1-4}$ alkyl and $C_{1-4}$ alkoxy;

$R^3$ is a group $ZR^4$ wherein Z is joined to $R^4$ through a $(CH_2)p$ group in which p is 0, 1 or 2 and Z represents a group $V(CH_2)$, $V(CF_2)$, $(CH_2)V$, $(CF_2)V$, $V(CRR')$, $V(CHR)$ or V where R and R' are each $C_{1-4}$ alkyl and in which V is a hydrocarbyl group containing 0,1 or 2 carbon atoms, carbonyl, dicarbonyl, CH(OH), CH(CN), sulphonamide, amide, O, $S(O)_m$ or $NR^b$ where $R^b$ is hydrogen or $R^b$ is $C_{1-4}$ alkyl; and $R^4$ is an optionally substituted $C_{3-6}$ cycloalkyl or an optionally substituted 5, 6, 7, 8, 9 or 10-membered carbocyclic or heterocyclic moiety; or $R^3$ is a group $ZR^4$ in which Z is $NR^b$, and $NR^b$ and $R^4$ together form an optionally substituted 5, 6, 7, 8, 9 or 10-membered carbocyclic or heterocyclic moiety;

each $R^5$ is independently selected from the group comprising; hydrogen, hydroxy, halogen, $C_{1-4}$ alkyl, $C_{1-4}$ alkoxy, $C_{1-4}$ alkylamino, di-[$C_{1-4}$ alkyl]amino, $C_{1-4}$ alkylthio, $C_{1-4}$ alkylsulphinyl, $C_{1-4}$ alkylsulphonyl, $C_{1-4}$ alkylcarbonyl, $C_{1-4}$ alkylcarbamoyl, di-[$C_{1-4}$ alkyl] carbamoyl, carbamyl, $C_{1-4}$ alkoxycarbonyl, cyano, nitro and trifluoromethyl, and n is 1,2 or 3.

Heterocyclic groups comprise one or more rings which may be saturated, unsaturated, or aromatic and which may independently contain one or more heteroatoms in each ring.

Carbocyclic groups comprise one or more rings which may be independently saturated, unsaturated or aromatic and which contain only carbon and hydrogen.

Suitably the 5, 6, 7, 8, 9 or 10-membered heterocyclic moiety is selected from the group comprising: furan, dioxolane, thiophene, pyrrole, imidazole, pyrrolidine, pyran, pyridine, pyrimidine, morpholine, piperidine, oxazole, isoxazole, oxazoline, oxazolidine, thiazole, isothiazole, thiadiazole, benzofuran, indole, isoindole, quinazoline, quinoline, isoquinoline and ketal.

Suitably the the 5, 6, 7, 8, 9 or 10-membered carbocyclic moiety is selected from the group comprising: phenyl, benzyl, indene, naphthalene, tetralin, decalin, cyclopentyl, cyclopentenyl, cyclohexyl, cyclohexenyl, and cycloheptyl.

By halo is meant fluoro, chloro, bromo or iodo.

Alkyl groups containing three or more carbon atoms may be straight, branched or cyclised.

In an embodiment, X is N.

In a further embodiment,

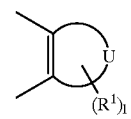

is selected from the group comprising:

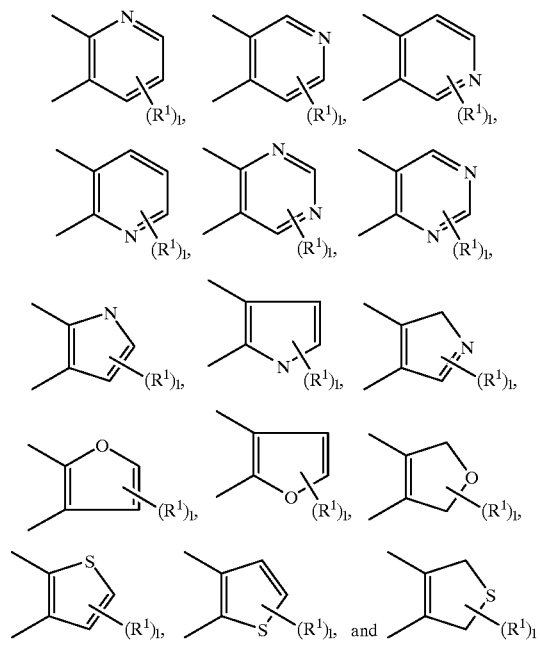

In a preferred embodiment,

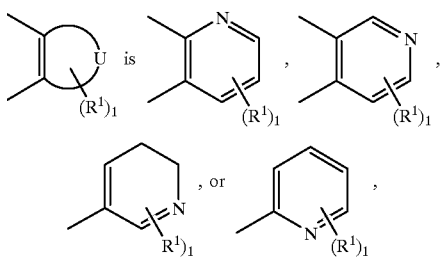

and l=0, 1 or 2.

In a further preferred embodiment,

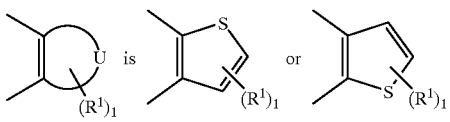

and l=0, 1 or 2.

In a further embodiment, Y is $NR^b$, $NR^b(CH_2)$, or $(CH_2)NR^b$; preferably Y is $NR^b$, and $R^b$ is preferably hydrogen or methyl.

In a further embodiment $R^1$ is selected from the group comprising phenyl, furan, thiophene, pyrrole, oxazole, isoxazole, thiazole, isothiazole, imidazole, pyrazole and piperazine or a hydrogenated derivative of any of the aforementioned and is optionally substituted by one or more groups selected from hydroxy, halogen, trifluoromethyl, trifluoromethoxy, nitro, amino, cyano, $C_{1-4}$ alkyl, $C_{1-4}$ alkoxy, $C_{1-4}$ alkylcarbonyl, $C_{1-4}$ alkoxycarbonyl, formyl or carboxy;

or $R^1$ is independently selected from the group comprising amino, hydrogen, halogen, hydroxy, nitro, $C_{1-8}$ alkyl, $C_{1-8}$ alkoxy, benzyloxy, morpholino, thiomorpholino, thiomorpholino-1,1-dioxide, pyrrolidino, piperidino, $C_{1-8}$ alkylthio, $C_{1-8}$ alkylsulphinyl, $C_{1-8}$ alkylsulphonyl, $C_{1-4}$ alkylamino, $C_{1-4}$ dialkylamino, [di-$C_{1-4}$ alkyl]amino-$C_{1-4}$ alkylene-($C_{1-4}$ alkyl)amino, $C_{1-4}$alkylamino-$C_{1-4}$alkylene-($C_{1-4}$alkyl)amino or hydroxy-$C_{1-4}$alkylene-($C_{1-4}$alkyl) amino.

In a preferred embodiment $R^1$ is selected from the group comprising phenyl, furan, pyrazole, imidazole and piperazine, optionally substituted by one or more groups selected from $C_{1-4}$ alkyl, formyl, carboxy or $C_{1-4}$ alkoxycarbonyl.

In a further preferred embodiment $R^1$ is independently selected from the group comprising hydrogen, halogen, $C_{1-4}$ alkyl, benzyloxy, thiomorpholino, thiomorpholino-1,1-dioxide, $C_{1-4}$ alkylamino, $C_{1-4}$ dialkylamino, [di-$C_{1-4}$ alkyl] amino-$C_{1-4}$ alkylene-($C_{1-4}$ alkyl)amino, $C_{1-4}$alkylamino-$C_{1-4}$alkylene-($C_{1-4}$alkyl)amino or hydroxy-$C_{1-4}$alkylene-($C_{1-4}$alkyl)amino.

In a further embodiment $R^2$ is hydrogen, $C_{1-4}$ alkyl, $C_{1-4}$ alkoxy or halogen, preferably hydrogen or methyl, more preferably hydrogen.

In a further embodiment $R^4$ is an optionally substituted 5 or 6-membered carbocyclic or heterocyclic moiety.

In a preferred embodiment $R^4$ is an optionally substituted phenyl, dioxolanyl, thienyl, cyclohexyl or pyridyl group.

In a further embodiment, Z is oxygen, $CH_2$, $NR^b$, $NR^b(CH_2)$, $(CH_2)NR^b$, $O(CH_2)$, $(CH_2)CN$, $O(CF_2)$, $(CH_2)O$, $(CF_2)O$, $S(CH_2)$, $S(O)_m$, carbonyl or dicarbonyl, wherein $R^b$ is hydrogen or $C_{1-4}$ alkyl.

In a preferred embodiment Z is oxygen, dicarbonyl, $OCH_2$, $CH_2(CN)$, $S(O)_m$ or $NR^b$, wherein $R^b$ is hydrogen or $C_{1-4}$ alkyl.

In a further embodiment, $R^3$ is benzyl, phenyl, pyridyl, pyridylmethyl, pyridyloxy, pyridyl methoxy, thienylmethoxy, dioxolanylmethoxy, cyclohexylmethoxy, phenoxy, phenylthio, benzyloxy, halo-, dihalo- and trihalobenzyloxy, $C_{1-4}$ alkoxybenzyloxy, phenyloxalyl or phenylsulphonyl.

In a further embodiment, $R^3$ is in the para position with respect to Y.

In a further embodiment $R^5$ is hydrogen, hydroxy, halogen, $C_{1-4}$ alkyl, $C_{1-4}$ alkoxy, di-[$C_{1-4}$ alkyl]amino, nitro or trifluoromethyl; in a preferred embodiment, $R^5$ is hydrogen, halogen, trifluoromethyl or methyl, more preferably hydrogen.

In a further embodiment, $(R^5)_n$ represents meta substituent(s) with respect to Y, and preferably n=1.

In an embodiment, the optional substituents for the carbocyclic or heterocyclic moiety, which may be present at any available position of said moiety, are selected from the group comprising: $(CH_2)_qS(O)_m$-$C_{1-4}$alkyl, $(CH_2)_qS(O)_m$-$C_{3-6}$cycloalkyl, $(CH_2)_qSO_2NR^8R^9$, $(CH_2)_qNR^8R^9$, $(CH_2)_qCO_2R^8$, $(CH_2)_qOR^8$, $(CH_2)_qCONR^8R^9$, $(CH_2)_qNR^8COR^9$, $(CH_2)_qCOR^8$, $(CH_2)_qR^8$, $NR^8SO_2R^9$ and $S(O)_mR^8$, wherein q is an integer from 0 to 4 inclusive; m is 0,1 or 2; $R^8$ and $R^9$ are independently selected from the group comprising hydrogen, $C_{1-4}$ alkyl, $C_{3-6}$ cycloalkyl, aryl, a 5- or 6-membered saturated or unsaturated heterocyclic ring which contains one or more heteroatoms which may be the same or different and which are selected from N, O or $S(O)_m$, with the proviso that the heterocyclic ring does not contain two adjacent O or $S(O)_m$ atoms.

In a further embodiment the optional substituents for the carbocyclic or heterocyclic moiety are selected from the group comprising morpholine, piperazine, piperidine, pyrrolidine, tetrahydrofuran, dioxolane, oxothiolane and oxides thereof, dithiolane and oxides thereof, dioxane, pyridine, pyrimidine, pyrazine, pyridazine, furan, thiofuran, pyrrole, triazine, imidazole, triazole, tetrazole, pyrazole, oxazole, oxadiazole and thiadiazole.

Other optional substituents for the carbocyclic or heterocyclic moiety and also for other optionally substituted groups include, but are not limited to, hydroxy, halogen, trifluoromethyl, trifluoromethoxy, nitro, amino, cyano, $C_{1-4}$ alkyl, $C_{1-4}$ alkoxy, $C_{1-4}$ alkylthio, $C_{1-4}$ alkylcarbonyl, carboxylate and $C_{1-4}$ alkoxycarboxyl.

Preferred compounds of the present invention include:
4-(4-Benzyloxyanilino)-6-chloropyrido[3,4-d]pyrimidine;
4-(4-Benzyloxyanilino)-6-(N-methylimidazol-5-yl)pyrido [3,4-d]pyrimidine;
4-(4-Benzyloxyanilino)-6-(N-methylimidazol-2-yl)pyrido [3,4-d]pyrimidine;
4-(4-Benzyloxyanilino)-6-(N-methylpyrazol-2-yl)pyrido[3, 4-d]pyrimidine;
4-(4-Benzyloxyanilino)-6-(furan-2-yl)pyrido[3,4-d] pyrimidine;
4-(4-Benzyloxyanilino)-6-(5-formylfuran-2-yl)pyrido[3,4-d]pyrimidine;
4-(4-Benzyloxyanilino)-6-(N,N-dimethylamino)pyrido[3,4-d]pyrimidine;
4-(4-Benzyloxyanilino)-6-(1-methylpiperazin-4-yl)-pyrido [3,4-d]pyrimidine;
4-(4-Benzyloxyanilino)-6-[(1-t-butoxycarbonyl)piperazin-4-yl]-pyrido[3,4-d]pyrimidine;
4-(4-Benzyloxyanilino)-6-(thiomorpholin-4-yl)-pyrido[3,4-d]pyrimidine;
4-(4-Benzyloxyanilino)-6-(thiomorpholine-1,1-dioxide-4-yl)-pyrido[3,4-d]pyrimidine;
6-N,N-Dimethylamino-4-(4-phenoxyanilino)pyrido[3,4-d] pyrimidine;
6-Chloro-4-(4-phenylthioanilino)pyrido[3,4-d]pyrimidine;
6-Chloro-4-(4-phenylsulphonylanilino)pyrido[3,4-d] pyrimidine;
6-(N,N-Dimethylamino)-4-(4-phenylsulphonylanilino) pyrido[3,4-d]pyrimidine;
6-(1-Methylpiperazin-4-yl)-4-(4-phenylsulphonylanilino)-pyrido[3,4-d]pyrimidine;
6-[N-Methyl-N-(2-dimethylaminoethyl)amino]-4-(4-phenylsulphonylanilino)pyrido[3,4-d]pyrimidine;

6-[N-Methyl-N-(2-hydroxyethyl)amino]-4-(4-phenylsulphonylanilino)pyrido[3,4-d]pyrimidine;
6-Chloro-4-[4-(1,3-dioxolan-2-yl)methoxyanilino]pyrido[3,4-d]pyrimidine;
6-(N,N-Dimethylamino)-4-[4-(1,3-dioxolan-2-yl)methoxyanilino]pyrido[3,4-d]pyrimidine;
6-Benzyloxy-4-(4-benzyloxyanilino)pyrido[3,4-d]pyrimidine;
4-(4-Benzyloxyanilino)pyrido[2,3-d]pyrimidine;
4-(4-Benzyloxyanilino)thieno[3,2-d]pyrimidine;
4-[3-Chloro-4-(2-methoxybenzyloxy)anilino]thieno[3,2-d]pyrimidine;
4-[3-Chloro-4-(2-fluorobenzyloxy)anilino]thieno[3,2-d]pyrimidine;
4-[4-(2-Bromobenzyloxy)-3-chloroanilino]thieno[3,2-d]pyrimidine;
4-[3-Methoxy-4-(2-methoxybenzyloxy)anilino]thieno[3,2-d]pyrimidine;
4-(4-Benzylanilino)thieno[3,2-d]pyrimidine;
4-(4-Phenoxyanilino)thieno[3,2-d]pyrimidine;
4-(4-(a,a-Difluorobenzyloxy)anilino)thieno[3,2-d]pyrimidine;
4-[4-(2-Thienylmethoxy)anilino]thieno[3,2-d]pyrimidine;
4-(4-Cyclohexylmethoxyanilino)thieno[3,2-d]pyrimidine;
7-Methyl-4-(4-phenoxyanilino)thieno[3,2-d]pyrimidine;
4-(4-Benzyloxy-3-trifluoromethylanilino)-7-methylthieno[3,2-d]pyrimidine;
4-[3-Chloro-4-(2-fluorobenzyloxy)anilino]-5-methylthieno[2,3-d]pyrimidine;
4-(4-Cyclohexylmethoxyanilino)-5-methylthieno[2,3-d]pyrimidine;
5-Methyl-4-(4-phenoxyanilino)thieno[2,3-d]pyrimidine;
4-(4-Phenoxyanilino)-5-(2-thienyl)thieno[2,3-d]pyrimidine;
4-(4-Benzyloxy-3-chloroanilino)-6-(N,N-dimethylamino)pyrido[3,4-d]pyrimidine;
6-(N,N-Dimethylamino)-4-(4-[1-phenyl-1-cyanomethyl]anilino)pyrido[3,4-d]pyrimidine;
6-(N,N-Dimethylamino)-4-[4-(1-phenyl-1,2-dioxoethyl-2-yl)anilino]-pyrido[3,4-d]pyrimidine;
6-(N,N-Dimethylamino)-4-[4-(pyridyl-2-methoxy)anilino]-pyrido[3,4-d]pyrimidine;
6-(N,N-Dimethylamino)-4-[4-(2-fluorobenzyloxy)anilino]pyrido[3,4-d]pyrimidine;
6-(N,N-Dimethylamino)-4-[4-(3-fluorobenzyloxy)anilino]pyrido[3,4-d]pyrimidine;
and salts thereof, particularly pharmaceutically acceptable salts thereof.

Other preferred compounds of the present invention include:
4-(4-Phenylsulphonylanilino)-6-(1-methylimidazol-2-yl)-pyrido[3,4-d]pyrimidine;
4-(4-Benzyloxyanilino)-7-dimethylamino-pyrido[4,3-d]pyrimidine;
4-(4-Benzyloxyanilino)-6-(2-imidazolyl)-pyrido[3,4-d]pyrimidine;
4-(4-Benzyloxyanilino)-6-(5-carboxyfuran-2-yl)-pyrido[3,4-d]pyrimidine;
and salts thereof, particularly pharmaceutically acceptable salts thereof.

Especially preferred compounds of the present invention include:
4-(4-Benzyloxyanilino)-6-(N-methylimidazol-5-yl)pyrido[3,4-d]pyrimidine;
4-(4-Benzyloxyanilino)-6-(N,N-dimethylamino)pyrido[3,4-d]pyrimidine;
6-(N,N-Dimethylamino)-4-[4-(1,3-dioxolan-2-yl)methoxyanilino]pyrido[3,4-d]pyrimidine;
and salts thereof, particularly pharmaceutically acceptable salts thereof.

Certain compounds of the formula (A) contain asymmetric carbon atoms and are, therefore, capable of existing as optical isomers. The individual isomers and mixtures of these are included within the scope of the present invention. Likewise, it is understood that compounds of formula (A) may exist in tautomeric forms other than that shown in the formula.

Salts of the compounds of the present invention may comprise acid addition salts derived from a nitrogen in the compound of formula (A). The therapeutic activity resides in the moiety derived from the compound of the invention as defined herein and the identity of the other component is of less importance although for therapeutic and prophylactic purposes it is, preferably, pharmaceutically acceptable to the patient. Examples of pharmaceutically acceptable acid addition salts include those derived from mineral acids, such as hydrochloric, hydrobromic, phosphoric, metaphosphoric, nitric and sulphuric acids, and organic acids, such as tartaric, acetic, trifluoroacetic, citric, malic, lactic, fumaric, benzoic, glycollic, gluconic, succinic and methanesulphonic and arylsulphonic, for example p-toluenesulphonic, acids.

In a further aspect, the present invention provides a process for the preparation of a compound of the formula (A), or a pharmaceutically acceptable salt thereof, which process comprises the reaction of a compound of the formula (B):

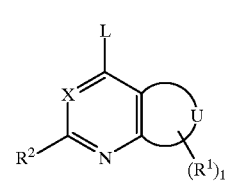

(B)

with a compound of the formula C:

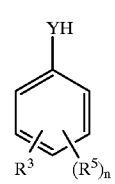

(C)

wherein L is a leaving group and X, Y and $R^1$ to $R^5$ are as hereinbefore defined. Suitable leaving groups will be well known to those skilled in the art and include, for example, halo such as chloro and bromo; sulphonyloxy groups such as methanesulphonyloxy and toluene-p-sulphonyloxy; and alkoxy groups.

The reaction is conveniently carried out in the presence of a suitable inert solvent, for example a $C_{1-4}$ alkanol, such as isopropanol, a halogenated hydrocarbon, an ether, an aromatic hydrocarbon or a do polar aprotic solvent such as acetone or acetonitrile at a non-extreme temperature, for example from 0 to 150° C., suitably 10 to 100° C., preferably 50 to 100° C.

Optionally, the reaction is carried out in the presence of a base when Y=NH. Examples of suitable bases include an organic amine such as triethylamine, or an alkaline earth metal carbonate, hydride or hydroxide, such as sodium or potassium carbonate, hydride or hydroxide. When YH=OH or SH it is necessary to perform the reaction in the presence of a base, and in such a case the product is not obtained as the salt.

The compound of formula (A) in the case in which Y=NR$^b$ may be obtained from this process in the form of a salt with the acid HL, wherein L is as hereinbefore defined, or as the free base by treating the salt with a base as hereinbefore defined.

The preparation of compounds (B) and (C) is well known to those skilled in the art.

In addition to the above, one compound of formula (A) may be converted to another compound of formula (A) by chemical transformation of the appropriate substituent or substituents using appropriate chemical methods (see for example, J.March "Advanced Organic Chemistry", Edition III, Wiley Interscience, 1985).

For example, a group $R^1$ may be substituted onto the ring U by replacement of another group $R^1$ which is a suitable leaving group. This is especially suitable for preparing compounds of formula (A) wherein an $R^1$ group is linked to the ring by a nitrogen atom; such compounds may, for example, be obtained by reaction of the amine corresponding to the group $R^1$ with the corresponding compound of formula (A) carrying a halo substituent in the appropriate position on the ring. This is also especially suitable for preparing compounds where $R^1$ is a heterocyclic ring system; such compounds may, for example, be prepared by reaction of the corresponding heteroaryl stannane derivative with the corresponding compound of formula (A) carrying a halo substituent in the appropriate position on the ring using a suitable catalyst such as an organometallic compound of palladium (for example bis(triphenylphosphine) palladium chloride) together with any other required catalytic additives.

A compound containing an alkyl or aryl mercapto group may be oxidised to the corresponding sulphinyl or sulphonyl compound by use of an organic peroxide (eg benzoyl peroxide) or suitable inorganic oxidant (eg OXONE®).

A compound containing a nitro substituent may be reduced to the corresponding amino-compound, eg by use of hydrogen and an appropriate catalyst (if there are no other susceptible groups) or by use of Raney Nickel and hydrazine hydrate.

Amino or hydroxy substituents may be acylated by use of an acid chloride or an anhydride under appropriate conditions. Equally an acetate or amide group may be cleaved to the hydroxy or amino compound respectively by treatment with, for example, dilute aqueous base.

In addition reaction of an amino substituent with triphosgene and another amine (eg aqueous ammonia, dimethylamine) gives the urea substituted product.

An amino substituent may also be converted to a dimethylamino substituent by reaction with formic acid and sodium cyanoborohydride.

All of the above-mentioned chemical transformations may also be used to convert one compound of formula (B) to a further compound of formula (B) prior to the reaction with the compound of formula (C); or to convert one compound of formula (C) to a further compound of formula (C) prior to the reaction with the compound of formula (B). The substituents present on the compounds (B) and (C) must be compatible with the conditions for their reaction together.

The present invention also provides compounds of formula (A) and pharmaceutically acceptable salts thereof (hereinafter identified as the 'active ingredients') for use in medical therapy, and particularly in the treatment of disorders mediated by aberrant protein tyrosine kinase activity such as human malignancies and the other disorders mentioned above. The compounds are especially useful for the treatment of disorders caused by aberrant c-erbB-2 activity such as breast, ovarian, non-small cell lung, pancreatic, gastric and colon cancers.

A further aspect of the invention provides a method of treatment of a human or animal subject suffering from a disorder mediated by aberrant protein tyrosine kinase activity which comprises administering to the human or animal subject an effective amount of a compound of formula (A) or a pharmaceutically acceptable salt thereof.

A further aspect of the present invention provides the use of a compound of formula (A), or a pharmaceutically acceptable salt thereof, in therapy.

A further aspect of the present invention provides the use of a compound of formula (A), or a pharmaceutically acceptable salt thereof, in the preparation of a medicament for the treatment of malignant tumours.

A further aspect of the present invention provides the use of a compound of formula (A), or a pharmaceutically acceptable salt thereof, in the preparation of a medicament for the treatment of atherosclerosis, resterosis or thrombosis.

Whilst it is possible for the compounds or salts of the present invention to be administered as the new chemical, it is preferred to present them in the form of a pharmaceutical formulation.

According to a further feature of the present invention we provide pharmaceutical formulations comprising at least one compound of the formula (A), or pharmaceutically acceptable salt(s) thereof, together with one or more pharmaceutically acceptable carriers, diluents or excipients.

Pharmaceutical formulations may be presented in unit dose forms containing a predetermined amount of active ingredient per unit dose. Such a unit may contain for example 0.5 mg to 1 g, preferably 5 mg to 100 mg of a compound of the formula (A) depending on the condition being treated, the route of administration and the age, weight and condition of the patient.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Preferred unit dosage formulations are those containing a daily dose or sub-dose, as herein above recited, or an appropriate fraction thereof, of an active ingredient.

It should be understood that in addition to the ingredients particularly mentioned above, the formulations may include other agents conventional in the art having regard to the type of formulation in question, for example those suitable for oral administration may include flavouring agents.

The compounds of the formula (A) and salts thereof have anticancer activity as demonstrated hereinafter by their inhibition of the protein tyrosine kinase c-erbB-2 enzyme. It has thus been established that compounds of the present invention are of use in medicine and, in particular in the treatment of certain human malignancies, for example breast, ovarian non-small cell lung, pancreatic, gastric and colon cancers. Accordingly, the present invention provides a method for the treatment of susceptible malignancies in an animal, e.g. a human, which comprises administering to the animal a therapeutically effective amount of a compound or salt of the present invention. In the alternative, there is also provided a compound or salt of the present invention for use in medicine and, in particular, for use in the treatment of cancers.

The present invention also provides the use of a compound of formula (A) or a salt thereof for the manufacture of a medicament for treatment of malignant tumours.

The animal requiring treatment with a compound or salt of the present invention is usually a mammal, such as a human being.

A therapeutically effective amount of a compound or salt of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of the present invention for the treatment of neoplastic growth, for example colon or breast carcinoma will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt of the present invention may be determined as a proportion of the effective amount of the compound per se.

Certain embodiments of the present invention will now be illustrated by way of example only. The physical data given for the compounds exemplified is consistent with the assigned structure of those compounds.

IR spectra were recorded on a Perkin-Elmer 257 grating spectrophotometer or a Bruker FS66 spectrophotometer.

1H NMR spectra were obtained on a Bruker WM 360-NMR spectrophotometer at 360 MHz, or on a Bruker AC250 spectrophotometer at 250 MHz. J values are given in Hz.

Mass spectra were obtained on one of the following machines: Varian CH5D (El), Kratos Concept (El), Kratos Ms50 (FAB), VG Micromass Platform (electrospray positive or negative), HP5989A Engine (thermospray positive).

Analytical thin layer chromatography (talc) was used to verify the purity of some intermediates which could not be isolated or which were too unstable for full characterisation, and to follow the progess of reactions. Unless otherwise stated, this was done using silica gel (Merck Silica Gel 60 F254).

Unless otherwise stated, column chromatography for the purification of some compounds used Merck Silica gel 60 (Art. 1.09385, 230–400 mesh), and the stated solvent system under pressure.

Petrol refers to petroleum ether, either the fraction boiling at 40–60° C., or at 60–80° C.

Ether refers to diethylether.

DMF refers to dimethylformamide.

DMSO refers to dimethylsulphoxide

Preparation of Intermediates

5-[(N-tert-Butoxycarbonyl)amino]-2-chloropyridine

A stirred solution of 6-chloronicotinic acid (47.3 g), diphenylphosphoryl azide (89.6 g) and triethylamine (46 ml) in t-butanol (240 ml) was heated at reflux under nitrogen for 2.5 hours. The solution was cooled and concentrated in vacuo. The syrupy residue was poured into a rapidly stirred solution of 0.5N aqueous sodium carbonate (2L). The precipitate was stirred for one hour and filtered. The solid was washed with water and dried in vacuo at 70° C. to give the title compound (62 g) as a pale brown solid, m.p. 144–146° C.: $\delta$H [$^2$H$_6$]-DMSO 8.25 (1H,d), 7.95 (1H,bd), 7.25 (1H,d), 6.65 (1H,bs), 1.51 (9H,s); m/z (M+1)$^+$229.

This material was carried forward to give 6-chloro-3H-pyrido[3,4-d]pyrimidin-4-one and 4,6-dichloropyrido[3,4-d]pyrimidine according to the procedures described for these compounds in WO95/19774

6-(N,N-Dimethylamino)-3H-pyrido[3,4-d]pyrimidin-4-one

6-Chloro-3H-pyrido[3,4-d]pyrimidin-4-one was reacted with dimethylamine (2.0 molar solution in methanol) in a pressure vessel at 130° C. for 32 hours. The reaction mixture was concentrated in vacuo and the resulting solid washed with ethyl acetate. This solid was heated in 2-propanol to give a suspension, which was filtered. The filtrate was concentrated in vacuo to give the product (60%).

4-Chloro-6-(N,N-dimethylamino)-pyrido[3,4-d]pyrimidine 6-(N,N-Dimethylamino)-3H-pyrido[3,4-d]pyrimidin-4-one (1.0 g, 5.25 mmol) was heated at reflux with phosphorous oxychloride (8.5 ml) and triethylamine (5.3 ml) for 3 hours. The mixture was concentrated in vacuo, azeotroping with toluene twice. The residue was partitioned between ethyl acetate and aqueous sodium hydrogen carbonate (8%), the layers separated, and the aqueous extracted once more with ethyl acetate. The combined organics were washed with water and brine, dried (sodium sulphate), and concentrated in vacuo. The residue was triturated with hexane to give the product as a solid (0.36 g, 33%).

General Procedures (A) Reaction of an amine with a bicyclic species containing a 4-chloropyrimidine ring The optionally substituted bicyclic species and the specified amine were mixed in an appropriate solvent (acetonitrile unless otherwise specified), and heated to reflux. When the reaction was complete (as judged by TLC), the reaction mixture was allowed to cool. The resulting suspension was diluted, e.g. with acetone, and the solid collected by filtration, washing e.g. with excess acetone, and dried at 60° C. in vacuo, giving the product as the hydrochloride salt. If the free base was required (e.g. for further reaction), this was obtained by treatment with a base e.g. triethylamine; purification by chromatography was then performed, if required.

(B) Reaction of a product from Procedure (A) with a heteroaryl tin reagent

A stirred mixture of the product from Procedure (A), (containing a suitable leaving group such as a chloro or bromo), a heteroaryl stannane and bis(triphenylphosphine) palladium dichloride were heated at reflux in dry dioxane under nitrogen for 24 hours. The resulting mixture was generally purified by chromatography on silica.

(C) Reaction of the product from Procedure (A) with a second amine

The product of Procedure (A) (containing a suitable leaving group such as chloro) was dissolved in an excess of the desired amine (or a solution thereof) and heated in a pressure vessel (e.g. at 130° C. for 17 hr). The cooled mixture was generally purified by chromatography on silica.

(D) Preparation of a substituted aniline

An appropriately substituted 4-nitrophenol was heated with an appropriately substituted benzyl halide (1.05 equiv.) and potassium carbonate (3 equiv.) in acetonitrile at reflux until reaction was complete (as judged by TLC). After standard work-up, the 4-benzyloxy-1-nitrobenzene was purified by column chromatography. Reduction using hydrogen at atmospheric pressure and a suitable catalyst (Pt/C or PdlC) in an appropriate solvent gave the corresponding 4-benzyloxyaniline, which was generally purified by column chromatography.

EXAMPLES

Example 1

4-(4-Benzyloxyanilino)-6-chloropyrido[3,4-]pyrimidine hydrochloride

Prepared according to Procedure A from 4-benzyloxyaniline and 4,6-dichloropyrido[3,4-d]pyrimidine; δH (CDCl$_3$) 9.11 (1H,s), 8.78 (1H,s), 7.75 (1H,d), 7.56 (2H,dd), 7.40 (5H,m), 7.15 (2H,d), 5.10 (2H,s); m/z (M+1)$^+$409.

Example 2

4-(4-Benzyloxyanilino)-6-(N-methylimidazol-5-yl)pyrido[3,4-d]pyrimidine

Prepared according to Procedure B from 4-(4-benzyloxyanilino)-6-chloropyrido[3,4-d]pyrimidine and 5-(tri-n-butylstannyl)-N-methylimidazole (prepared according to the published method: *Acta Chem. Scand.*, (1993), 47(1), 57); δH [$^2$H$_6$]-DMSO 10.00 (1H,s), 9.15 (1H,s), 8.65 (1H,s), 8.60 (1H, s), 7.80 (1H,s), 7.61(2H,d), 7.50 (1H,s), 7.25–7.49 (5H,m), 7.10 (2H,d), 5.13 (2H,s), 3.98 (3H,s); m/z (M+1)$^+$409.

Example 3

4-(4-Benzyloxyanilino)-6-(N-methylimidazol-2-yl)pyrido[3,4-d]pyrimidine

Prepared according to Procedure B from 4-(4-benzyloxyanilino)-6-chloropyrido[3,4-d]pyrimidine and 2-(tri-n-butylstannyl)-N-methylimidazole (prepared according to the published method: *J. Organometallic Chem.*, (1989), 61); δH [$^2$H$_6$]-DMSO 10.35 (1H,s), 9.17 (1H,s), 9.13 (1H,s), 8.65 (1H, s), 7.79 (2H,d), 7.32–7.55 (6H,m), 7.13 (1H,s), 7.09 (2H,d), 5.16 (2H,s), 4.10 (3H,s); m/z (M+1)$^+$409.

Example 4

4-(4-Benzyloxyanilino)-6-(N-methylpyrazol-2-yl)pyrido[3,4-d]pyrimidine

Prepared according to Procedure B from 4-(4-benzyloxyanilino)6-chloropyrido[3,4-d]pyrimidine and 2-(tri-n-butylstannyl)-N-methylpyrazole (prepared according to the published method: WO 94/00825); δH [$^2$H$_6$]-DMSO 9.30 (1H,s), 8.80 (2H,m), 7.80 (2H,d), 7.65 (1H,d), 7.50 (6H,m), 7.20 (2H,d), 6.90 (1H,d), 5.20 (2H,s), 4.25 (3H,s); m/z (M+1)$^+$409.

Example 5

4-(4-Benzyloxyanilino)-6-(furan-2-yl)pyrido[3,4-d]pyrimidine

Prepared according to Procedure B from 4-(4-benzyloxyanilino)-6-chloropyrido[3,4-d]pyrimidine and 2-(tri-n-butylstannyl)furan (Aldrich); δH [$^2$H$_6$]-DMSO 9.08 (1H,s), 8.70 (1H,s), 8.55 (1H,s), 7.90 (1H,d), 7.69 (2H, d), 7.40 (5H,m), 7.10 (1H,d), 7.03 (2H,d), 6.69 (1H,m), 5.10 (2H,s); m/z (M+1)$^+$395.

Example 6

4-(4-Benzyloxyanilino)-6-(5-formylfuran-2-yl)pyrido[3,4-d]pyrimidine 4-(4-Benzyloxyanilino)-6-chloropyrido[3,4-d]pyrimidine (4.0 g, 110 mmol), 2-(1,3-dioxolan-2-yl)-5-(tributylstannyl) furan (*J. Chem. Soc., Chem Commun.*, (1988), 560) (6.0 g, 14.0 mmol) were reacted together according to Procedure B for 20 hrs. The reaction mixture was allowed to cool, 1N HCl (50 ml) added and stirred at RT for 15 minutes. The reaction was filtered and the residue washed with dioxane (20 ml) and 2N HCl (20 ml). The combined filtrate and washings were stirred at RT for a further hour. The dioxane was removed under vacuum, the reaction diluted with water and the solid which precipitated was collected by filtration, and washed with water, iso-hexane and acetone. This precipitate was converted to the free base by partitioning into a mixture of triethylamine, ethyl acetate and water. The organic phase was washed with water, dried (magnesium sulphate) and the solvent removed under vacuum. The residue was triturated with iso-hexane/ethyl acetate to give the product (2.41 g, 52%) as a yellow solid; δH [$^2$H$_6$]-DMSO 10.60 (1H, b, NH), 9.83 (1H, s, CHO), 9.30 (1H, s, 2-H), 9.08 (1H, s, 5-H or 8-H), 8.76 (1H, s, 5-H or 8-H), 7.89 (1H, d, furan-H), 7.82 (2H, d, 2'-H, 6'-H), 7.65–7.42 (6H, m, 5x Ph-H, furan-H), 7.21 (2H, d, 3'-H, 5'-H), 5.26 (2H, s, OCH$_2$); m/z (M+1)$^+$423

Example 7

4-(4-Benzyloxyanilino)-6-(N,N-dimethylamino)pyrido[3,4-d]pyrimidine

Prepared according to Procedure C from 4-(4-benzyloxyanilino)-6-chloropyrido[3,4-d]pyrimidine and dimethylamine (33% aqueous solution); δH (CDCl$_3$) 9.00 (1H,s), 8.52 (1H,s), 7.59 (2H,d), 7.40 (4H,m), 7.23 (1H,s), 7.13 (2H,d), 6.35 (1H,s), 5.10 (2H,s), 3.20 (6H,s); m/z (M+1)$^+$395.

Example 8

4-(4-Benzyloxyanilino)-6-(1-methylpiperazin-4-yl)-pyrido[3,4-d]pyrimidine

Prepared according to Procedure C from 4-(4-benzyloxyanilino)-6-chloropyrido[3,4-d]pyrimidine and 1-methylpiperazine; δH (CDCl$_3$) 9.00 (1H,s), 8.58 (1H,s), 7.59 (2H, d), 7.28–7.40 (5H,m), 7.02 (2H,d), 6.59 (1H,s), 5.08 (2H,s), 3.60–3.74 (4H,m), 2.52–2.64 (4H,m), 2.40 (3H,s); m/z (M+1)$^+$427.

Example 9

4-(4-Benzyloxyanilino)-6-[(1-t-butoxycarbonyl)piperazin-4-yl]-pyrido[3,4-d]pyrimidine Prepared according to Procedure C from 4-(4-benzyloxyanilino)-6-chloropyrido[3,4-d]pyrimidine and (1-t-butoxycarbonyl)piperazine (commercially available from Aldrich); tlc (dichloromethane:ethanol:aq.ammonia, 100:8:1) Rf 0.44; m/z (M+1)$^+$513.

Example 10

4-(4-Benzyloxyanilino)-6-(thiomorpholin-4-yl)-pyrido[3,4-d]pyrimidine

Prepared according to Procedure C from 4-(4-benzyloxyanilino)-6-chloropyrido[3,4-d]pyrimidine and thiomorpholine; δH (CDCl$_3$) 9.00 (1H,s), 8.59 (1H,s), 7.59 (2H, d), 7.28–7.50 (5H,m), 7.03 (2H,d), 6.56 (1H,s), 5.09 (2H,s), 3.92–4.18 (4H,m), 2.62–2.92 (4H,m); m/z (M+1)$^+$430.

Example 11

4-(4-Benzyloxyanilino)-6-(thiomorpholine-1,1-dioxide-4-yl)-pyrido[3,4-d]pyrimidine 4-(4-Benzyloxyanilino)-6-(thiomorpholin-4-yl)-pyrido[3,4-d]pyrimidine (0.075 g, 0.175 mmol) was dissolved in a mixture of methanol (20 ml) and water (10 ml) and reacted with Oxone® (2KHSO$_5$.KHSO$_4$. K$_2$SO$_4$, 0.323 g, 0.525 mmol) at room temperature for 24 h to give the product as a yellow solid (0.023 g, 28%); δH (CDCl$_3$) 10.17 (1H,s), 9.65 (1H,s), 9.04 (1H,s), 8.74 (1H,s), 7.73 (2H, d), 7.30–7.63 (5H,m), 7.03 (2H,d), 5.11 (2H,s), 5.02 (2H,t), 4.54 (2H,t), 3.44 (2H,d), 3.18 (2H,d); m/z (M+1)$^+$462.

Example 12

6-N,N-Dimethylamino-4-(4-phenoxyanilino)pyrido[3,4-d]pyrimidine

6-Chloro-4-(4-phenoxyanilino)pyrido[3,4-d]pyrimidine was prepared by the reaction of 4-phenoxyaniline and 4,6-dichloropyrido[3,4-d]pyrimidine in 2-propanol according to Procedure A, with triethylamine present to give the free base of the product directly. Reaction of this product with dimethylamine (33% aqueous solution) according to Procedure C gave the title compound: δH (CDCl$_3$) 9.00 (1H,s), 8.54 (1H,s), 7.70 (2H, d), 7.00–7.44 (5H,m), 7.13 (2H,d), 6.38 (1H,s), 3.22 (6H,s); m/z (M+1)$^+$358.

Example 13

6-Chloro-4-(4-phenylthioanilino)pyrido[3,4-d]pyrimidine hydochloride

Prepared according to Procedure A from 4-(phenylthio)aniline (commercially available from Salor) and 1,6-dichloropyrido[3,4-d]pyrimidine; δH [$^2$H$_6$]-DMSO 8.94 (1H,s), 8.85 (1H,s), 8.25 (1H,s), 7.96 (2H,d), 7.24–7.49 (7H,m); m/z (M+1)$^+$365.

Example 14

6-Chloro-4-(4-phenylsulphonylanilino)pyrido[3,4-d]pyrimidine hydochloride

Prepared according to Procedure A from 4-phenylsulphonylaniline (Helv. Chim. Acta., 1983, 66 (4), 1046) and 4,6-dichloropyrido[3,4-d]pyrimidine; δH [$^2$H$_6$]-DMSO 9.09 (1H,s), 8.80–8.88 (2H,m), 8.19 (2H,d), 7.94–8.09 (4H,m), 7.53–7.20 (3H,m); m/z (M+1)$^+$397.

Example 15

6-(N,N-Dimethylamino)-4-(4-phenylsulphonylanilino)pyrido[3,4-d]pyrimidine

Prepared according to Procedure C from 6-chloro-4-(4-phenylsulphonylanilino)-pyrido[3,4-d]pyrimidine and dimethylamine (33% aqueous solution); δH (CDCl$_3$) 9.00 (1H, s), 8.57 (1H,s), 7.78–8.00 (6H,m), 7.70 (1H,br s) 7.45–7.65 (3H,m), 6.50 (1H,s), 3.21 (6H,s); m/z (M+1)$^+$254.

Example 16

6-(1-Methylpiperazin-4-yl)-4-(4-phenylsulphonylanilino)-pyrido[3,4-d]pyrimidine Prepared according to Procedure C from 6-chloro-4-(4-phenylsulphonylanilino)pyrido[3,4-d]pyrimidine and 1-methylpiperazine; δH (CDCl$_3$+DMSO) 9.66 (1H,s), 8.91 (1H,s), 8.52 (1H,s), 8.15 (2H, d), 7.88–7.98 (4H,m), 7.48–7.62 (4H,m), 3.66–3.74 (4H,m), 2.52–2.64 (4H,m), 2.38 (3H,s); m/z (M+1)$^+$461.

Example 17

6-[N-Methyl-N-(2-dimethylaminoethyl)amino]-4-(4-phenylsulphonylanilino)-pyrido[3,4-d]pyrimidine Prepared according to Procedure C from 6-chloro-4-(4-phenylsulphonylanilino)-pyrido[3,4-d]pyrimidine and N,N, N'-trimethylethylenediamine; δH (CDCl$_3$) 8.92 (1H,s), 8.69 (1H,s), 8.49 (1H,s), 7.80–8.05 (6H,m), 7.38–7.60 (3H,m), 6.79 (1H,s), 3.68 (2H,t), 3.42 (3H,s), 2.51 (1H,t), 2.29 (6H,s); m/z (M+1)$^+$463.

Example 18

6-[N-Methyl-N-(2-hydroxyethyl)amino]-4-(4-phenylsulphonylanilino)pyrido[3,4-d]pyrimidine Prepared according to Procedure C from 6-chloro4-(4-phenylsulphonylanilino)-pyrido[3,4-d]pyrimidine and 2-(methylamino)ethanol; δH [$^2$H$_6$]-DMSO 9.99 (1H,s), 8.89 (1H,s), 8.48 (1H,s), 8.20 (2H,d), 7.97–8.09 (4H,m), 7.60–7.78 (3H,m), 7.27 (1H,s), 4.27 (1H,t), 3.75–3.85 (2H, m), 3.60–3.71 (2H,m), 3.21 (3H,s); m/z (M+1)$^+$436.

Example 19

6-Chloro-4-[4-(1,3-dioxolan-2-yl)methoxyanilino] pyrido[3,4-d]pyrimidine hydochloride Prepared according to Procedure A from 4-(1,3-dioxolan-2-yl)methoxyaniline (prepared according to the published method: WO 96/09294) and 4,6-dichloropyrido[3,4-d] pyrimidine; δH [$^2$H$_6$]-DMSO 9.06 (1H,s), 8.85 (1H,s), 8.79 (1H,s), 7.73 (2H,d), 7.05 (2H,d), 5.21 (1H,t), 3.70–4.06 (6H,m); m/z (M+1)$^+$359.

Example 20

6-(N,N-Dimethylamino)-4-[4-(1,3-dioxolan-2-yl) methoxyanilino]pyrido[3,4-d]pyrimidine Prepared according to Procedure C from 6-chloro-4-[4-(1,3-dioxolan-2-yl)methoxyanilino]pyrido[3,4-d]pyrimidin and dimethylamine (33% aqueous solution); δH (CDCl$_3$) 9.71 (1H,s), 8.87 (1H,s), 8.38 (1H,s), 7.78 (2H,d), 7.35 (1H,s) 7.09 (2H,d), 5.30 (1H,t), 4.00 (6H,m), 3.25 (6H,s); m/z (M+1)$^+$368.

Example 21

6-Benzyloxy-4-(4-benzyloxyanilino)pyrido[3,4-d] pyrimidine

6-Chloro-3H-pyrido[3,4-d]pyrimidine-4-one (9.08 g, 50.0 mmol) was reacted with sodium hydride (60% dispersion on mineral oil, 8.14 g, 203.5 mmol) in benzyl alcohol at 150° C. for 18 hours. The mixture was partitioned between water and ether (water layer at pH14 from the excess sodium hydride) and the layers separated. The aqueous layer was further washed with ether, and then acidified to pH1 with dilute HCl, giving a cream precipitate. This was collected by filtration and dried at 60° C. in vacuo to give 6-benzyloxy-3H-pyrido[3,4-d]pyrimidin-4-one (10.59 g, 84%); δH [$^2$H$_6$]-DMSO 8.71 (1H,s), 7.79 (1H,s), 7.25–7.48 (6H,m), 5.40 (2H,s); m/z (M+1)$^+$254. 6-Benzyloxy-3H-pyrido[3,4-d]pyrimidine-4-one (1.033 g, 4.08 mmol) was reacted with thionyl chloride (10 ml) and dimethyl formamide (2 drops) at reflux under a nitrogen atmosphere for 5 hours, and then left at room temperature overnight. The mixture was concentrated in vacuo, azeotroping twice with toluene to remove the excess thionyl chloride, to give 6-benzyloxy4-chloropyrido[3,4-d]pyrimidine; δH [$^2$H$_6$]-DMSO 8.73 (1H,s), 8.10 (1H,s), 7.25–7.55 (6H,m), 5.41 (2H,s). 6-Benzyloxy-4-chloropyrido[3,4-d]pyrimidine (ca. half the above material, ca. 2 mmol) was reacted with 4-benzyloxyaniline (0.430 g, 2.25 mmol) in acetonitrile (10 ml) according to Procedure A for 5 hours. The resulting brown solid was 6-benzyloxy4-(4-benzyloxyanilino)pyrido [3,4-d]pyrimidine (0.621 g, 71%); δH [$^2$H$_6$]-DMSO 8.99 (1H,s), 8.73 (1H,s), 8.22 (1H,s), 7.71 (2H,d), 7.15–7.55 (10H,m), 7.10 (2H,d), 5.50 (2H,s), 5.13 (2H, s); m/z (M+1)$^+$ 435.

Example 22

4-(4-Benzyloxyanilino)pyrido[2,3-d]pyrimidine

4-Chloropyrido[2,3-d]pyrimidine (prepared as described in: R. K. Robins and G. W. Hitchings, *J. Am. Chem. Soc,* 77, 2256 (1955)) (0.165 g, 1.0 mmol) and 4-benzyloxyaniline (0.199 g, 1.0 mmol) were reacted in ethanol (10 ml) for ca. 2 hours, according to Procedure A. After cooling, the mixture was filtered, treated with triethylamine and concentrated in vacuo. Purification by column chromatography on silica, eluting with methanol/chloroform (1:10), gave the product as a yellow solid (0.020 g, 6%) with m.p. 235–237° C.; (Found: C, 72.34; H, 4.85; N, 16.57. C$_{20}$H$_{16}$N$_4$O0.25H$_2$O requires: C, 72.16; H, 4.99; N, 16.83%); δH [$^2$H$_6$]-DMSO 9.10 (1H, d, J 9) and 9.08 (1H, d, J 5) (6H, 8-H), 8.78 (1H, s, 2-H), 7.76 (1H, dd, J 9, 5, 7-H), 7.62 (2H, d, J 9, 2'-H, 6'-H), 7.43 (2H, d, J 7, 2"-H, 6"-H), 7.38 (2H, t, J 7, 3"-H, 5"-H), 7.30 (1H, t, J 8, 4"-H), 7.08 (2H, d, J 9, 3'-H, 5'-H), 5.11 (2H, s, CH$_2$); m/z (%) 328 (68, M$^+$), 237 (100), 91 (64).

Example 23

4-(4-Benzyloxyanilino)thieno[3,2-d]pyrimidine hydrochloride

4-Chlorothieno[3,2-d]pyrimidine (commercially available from Maybridge Chemical Co. Ltd.) (0.400 g, 2.35 mmol) and 4-benzyloxyaniline (0.514 g, 2.50 mmol) were reacted in 2-propanol (10 ml) for 2.5 hours, according to Procedure A. The product was obtained as pale cream prisms (0.640 g, 74%) with m.p. 227–229° C.; (Found: C, 60.86; H, 4.19; N, 11.31. C$_{19}$H$_{15}$N$_3$OS.HCl.0.33H$_2$O requires: C, 60.71; H, 4.43; N, 11.19%); tlc (ethyl acetate) Rf 0.38; δH [$^2$H$_6$]-DMSO 11.32 (1H, br s, NH), 8.81 (1H, s, 2-H), 8.45 (1H, d, J 7, 6 H or 7 H) 7.28–7.62 (8H, m, 6H or 7H, 2'-H, 6'-H, 5 x PhH), 7.10 (2H, d, J 9, 3'-H, 5'-H), 5.15 (2H, s, CH$_2$); m/z (%) 333 (34, M$^+$), 242 (100), 91 (49).

Example 24

4-[3-Chloro-4-(2-methoxybenzyloxy)anilino]thieno [3,2-d]pyrimidine hydrochloride 4-Chlorothieno[3,2-d]pyrimidine (0.102 g, 0.60 mmol) and 3-chloro-4-(2-methoxybenzyloxy)aniline (prepared according to the published method: WO 96/09294) (0.161 g, 0.65 mmol) were reacted in 2-propanol (4 ml) for 1.25 hours, according to Procedure A. The product was obtained as pale cream prisms (0.203 g, 78%) with m.p. 210–212° C.; (Found: C, 55.28; H, 4.00; N, 9.44. C$_{20}$H$_{16}$ClN$_3$O$_2$S.HCl requires: C, 55.31; H, 3.92; N, 9.67%); δH [$^2$H$_6$]-DMSO 11.19 (1H, br s, NH), 8.88 (1H, s, 2-H), 8.48 (1H, d, J 7, 6 H or 7 H) 7.87 (1H, d, J 5, 2'-H), 7.55–7.62 (2H, m, 6'-H, 4"-H), 7.48 (1H, d, J 7, 6H or 7H), 7.28–7.40 (2H, m, 5'-H, 6"-H), 7.09 (1H, d, J 9, 3"-H), 7.00 (1H, t, J 9, 5"-H), 5.22 (2H, s, CH$_2$), 3.85 (3H, s, OCH$_3$).

Example 25

4-[3-Chloro-4-(2-fluorobenzyloxy)anilino]thieno[3, 2-d]pyrimidine hydrochloride

4-Chlorothieno[3,2-d]pyrimidine (0.103 g, 0.60 mmol) and 3-chloro-4-(2-fluorobenzyloxy)aniline (prepared according to the published method: WO 96/09294) (0.197 g, 0.78 mmol) were reacted in 2-propanol (4.5 ml) for 4.5 hours, according to Procedure A. The product was obtained as cream prisms (0.208 g, 82%) with m.p. 231–233° C.; (Found: C, 53.39; H, 3.30; N, 9.79. $C_{19}H_{13}ClFN_3OS.HCl.H_2O$ requires: C, 53.47; H, 3.42; N, 9.85%); δH [$^2H_6$]-DMSO 8.88 (1H, s, 2-H), 8.47 (1H, d, J 7, 6 H or 7 H) 7.88 (1H, d, J 5, 2'-H), 7.55–7.68 (3H, m), 7.33–7.49 (2H, m), 7.20–7.30 (2H, m) (6H or 7H, 5'-H, 6'-H, 3"-H, 4"-H, 5"-H, 6"-H), 5.29 (2H, s, $CH_2$); m/z 385 ($M+1^+$).

Example 26

4-[4-(2-Bromobenzyloxy)-3-chloroanilino]thieno[3,2-d]pyrimidine hydrochloride 4-Chlorothieno[3,2-d]pyrimidine (0.103 g, 0.60 mmol) and 4-(2-fluorobenzyloxy)-3-chloroaniline (prepared according to the published method: WO 96/09294) (0.234 g, 0.75 mmol) were reacted in 2-propanol (5 ml) according to Procedure A. The product was obtained as pale cream prisms (0.256 g, 88%) with m.p. 247–248° C.; (Found: C, 47.10; H, 2.91; N,9.03. $C_{19}H_{13}BrClN_3OS.HCl$ requires: C, 47.23; H, 2.92; N, 8.70%); δH [$^2H_6$]-DMSO 11.28 (1H, br s, N—H), 8.88 (1H, s, 2-H), 8.49 (1H, d, J 7, 6 H or 7 H) 7.89 (1H, d, J 5, 2'-H), 7.57–7.75 (4H, m), 7.44–7.53 (1H, m), 7.30–7.39 (2H, m) (6H or 7H, 5'-H, 6'-H, 3"-H, 4"-H, 5"-H, 6"-H), 5.29 (2H, s, $CH_2$); m/z 447 ($M^+$).

Example 27

4-[3-Methoxy-4-(2-methoxybenzyloxy)anilino]thieno[3,2-d]pyrimidine hydrochloride 4-Chlorothieno[3,2-d]pyrimidine (0.102 g, 0.60 mmol) and 3-methoxy-4-(2-methoxybenzyloxy)aniline (prepared according to the published method: WO 96/09294) (0.181 g, 0.70 mmol) were reacted in 2-propanol (3 ml) for 75 minutes according to Procedure A. The product was obtained as off-white prisms (0.211 g, 82%) with m.p. 207–208° C.; (Found: C, 58.55; H, 4.76; N, 9.53. $C_{21}H_{19}N_3O_3S.HCl$ requires: C, 58.55; H, 4.69; N, 9.77%); δH [$^2H_6$]-DMSO 8.85 (1H, s, 2-H), 8.41 (1H, d, J 7, 6 H or 7 H) 7.55 (1H, d, J 7, 6-H or 7-H), 7.42 (1H, d, J 9, 6'-H), 7.34 (1H, t, J 8, 4"-H), 7.29 (1H, s, 2'-H), 7.02–7.20 (3H, m, 5'-H, 3"-H, 6"-H), 6.98 (1H, t, J 8, 5"-H), 5.08 (2H, s, $CH_2$), 3.83 and 3.79 (2x 3H, 2 x s, 2 x $OCH_3$); m/z 393 ($M^+$).

Example 28

4-(4-Benzylanilino)thieno[3,2-d]pyrimidine hydrochloride

4-Chlorothieno[3,2-d]pyrimidine (0.060 g, 0.35 mmol) and 4-aminodiphenylmethane (commercially available from K & K) (0.080 g, 0.44 mmol) were reacted in 2-propanol (5 ml) for 30 minutes according to Procedure A. The white solid obtained was 4-(4-benzylanilino)thieno[3,2-d]pyrimidine hydrochloride (0.070 g, 56%), m.p. 251–255° C.; (Found: C, 64.00; H, 4.45, N, 11.72. $C_{19}H_{15}N_3S.HCl.0.1H_2O$ requires: C, 64.16; H, 4.59; N, 11.81%); δH [$^2H_6$]-DMSO 11.05 (1H, br s, NH), 8.81 (1H, s, 2-H), 8.43 (1H, d, J 8, 6-H or 7-H), 7.60–7.52 (3H, m, (6-H or 7-H), 2'-H, 6'-H), 7.35–7.20 (6H, m, 3'-H, 5'-H, 2"-H, 3"-H, 5"-H, 6"-H), 7.19 (1H, t, J 6, 4"-H), 3.95, (2H, s, $CH_2$); m/z (%) 318 (100, $M+1^+$); $n_{max}$ (KBr disc)/$cm^{-1}$ 2570, 1630, 1595, 1485, 1475, 1365.

Example 29

4-(4-Phenoxyanilino)thieno[3,2-d]pyrimidine hydrochloride

4-Chlorothieno[3,2-d]pyrimidine (0.085 g, 0.50 mmol) and 4-phenoxyaniline (0.105 g, 0.55 mmol) were reacted in 2-propanol (3.5 ml) for 3 hours according to Procedure A. The product was obtained as a cream solid (0.130 g, 73%), m.p. 236–240° C.; (Found: C, 60.61; H, 3.95, N, 11.93. $C_{18}H_{13}N_3OS.HCl$ requires: C, 60.76; H, 3.97; N, 11.81%); δH [$^2H_6$]-DMSO 10.93 (1H, br s, NH), 8.80 (1H, s, 2-H), 8.42 (1H, d, J 8, 6-H or 7-H), 7.69 (2H, d, J 9, 2'-H, 6'-H), 7.55 (1H, d, J 8, 6-H or 7-H), 7.41 (2H, t, J 9, 3"-H, 5"-H), 7.18 (1H, t, J 9, 4"-H), 7.04–7.15 (4H, m, 3'-H, 5'-H, 2"-H, 6"-H); m/z (%) 318 (100, $M-1^+$).

Example 30

4-(4-(a,a-Difluorobenzyloxy)anilino)thieno[3,2-d]pyrimidine hydrochloride

A mixture of 1,3 dibromo-5,5-dimethylhydantoin (11.5 g, 40.2 mmol), a,a-difluorotoluene (prepared by the published method of W. J. Middleton, *J. Org. Chem.*, 1975, 40, p574) (7.0 g, 55 mmol) and AIBN (0.25 g) in $CCl_4$ (300 ml) was heated at reflux for 10 h while being irradiated (tungsten filament lamp, 500W). The mixture was then diluted with petrol and the remaining precipitate removed by filtration. The filtrate was then evaporated and the resulting oil chromatographed (silica, petrol) to give a-bromo-a, a-difluorotoluene (5.5 g, 50%) as a colourless oil; δH [$^2H_6$]-DMSO 7.68 (2H, d, J 8, 2-H, 6-H), 7.62–7.55 (3H, m, 3-H, 4-H, 5-H); dC [$^2H_3$]-$CDCl_3$ 138.3 (triplet, J 23, 1-C), 131.2 (4-C), 128.6 (3-C and 5-C), 124.3 (2-C and 6-C), 118.6 (triplet, J 300, $CBrF_2$). This $^{13}C$ data agrees with that published by A. Haas et al., *Chem Ber.*, 1988, 121, p1329. 4-Nitrophenol (16.6 g, 0.119 mol) was added to a stirred solution of potassium hydroxide (7.0 g, 0.13 g) in absolute ethanol (50 ml) and the mixture was heated at reflux for 30 min. Diethyl ether was then added to this yellow mixture and the resulting yellow precipitate collected by filtration to give potassium 4-nitrophenoxide (19.5 g, 93%) as a bright yellow solid, which was used directly in the next step. A stirred mixture of potassium 4-nitrophenoxide (5.47 g, 31 mmol) and a-bromo-a,a-difluorotoluene (3.2 g, 15 mmol) in dry DMF (30 ml) under $N_2$ was heated at 78–80° C. for 8 h. The mixture was then concentrated in vacuo to remove most of the DMF, and the residue was partitioned between aq. sat. sodium bicarbonate (30 ml) and dichloromethane. The organic layer was separated and the water layer further extracted with dichloromethane (2×50 ml). The combined organics were washed with water and dried over $Na_2SO_4$. The solvents were then evaporated in vacuo and the residue chromatographed (silica, 10% diethyl ether/petrol) to give 4-(a,a-difluorobenzyloxy)nitrobenzene (2.7 g, 67%) as a white crystalline solid, m.p. 46–48° C.; δH [$^2H_6$]-DMSO 8.80 (2H, d, J 9, 2-H, 6-H), 7.78 (2H, d, J 9, 2'-H, 6'-H), 7.65–7.55 (5H, m, 3-H, 5-H, 3'-H, 4'-H, 5'-H); m/z (%) 265 (39, $M^+$), 246 (44), 127 (100). A solution of 4-(a,a-difluorobenzyloxy)nitrobenzene (0.65 g, 2.5 mmol) in a mixture of ethyl acetate (25 ml) and methanol (25 ml) was carefully added to 10% palladium on charcoal (50 mg). The resulting suspension was stirred at r.t.p. under an atmosphere of hydrogen. When the reaction was complete (as indicated by tlc and calculated uptake of hydrogen) the suspension was filtered through a pad of hyflo and the filtrate evaporated to dryness to give 4-(a,a-difluorobenzyloxy)aniline (0.56 g, 98%) as an off-white solid; δH [$^2H_6$]-DMSO 7.75 (2H, d, J 7, 2'-H, 6'-H), 7.62 (3H, m, 3'-H, 4'-H, 5'-H), 7.00 (2H, d, J 7, 2-H, 6-H), 6.60 (2H, d, J 7, 3-H, 5-H), 5.10 (2H, br s, $NH_2$); m/z (%) 235 (95, $M^+$), 127 (100). 4-Chlorothieno[3,2-d]pyrimidine (0.049 g, 0.29 mmol) and 4-(a,a-difluorobenzyloxy)aniline (0.085 g, 0.36 mmol) were reacted in 2-propanol (5 ml) for 30 minutes according to Procedure A. The white solid obtained was 4-(4-(a,a-difluorobenzyloxy)anilino)thieno[3,2-d]pyrimidine hydrochloride (0.053 g, 36%), m.p. 265° C. (dec); (Found: C, 56.57; H, 3.47, N, 10.42. $C_{19}H_{13}N_3SOF_2.HCl$ requires: C, 56.23; H, 3.48; N, 10.35%); δH [$^2H_6$]-DMSO 11.25 (1H, br s, NH), 8.88 (1H, s, 2-H), 8.50 (1H, d, J 5, 6-H or 7-H), 7.80–7.73 (4H, m, 2'-H, 6'-H, 2"-H, 6"-H); 7.67–7.55 (4H, m, 3"-H, 4"-H, 5"-H and (6-H or 7-H)), 7.40 (2H, d, J 9, 3'-H, 5'-H); m/z (%) 369 (60, M⁺), 242 (100); $n_{max}$ (KBr disc)/cm⁻¹ 2550, 1630, 1591, 1504, 1468, 1321.

Example 31

4-[4-(2-Thienylmethoxy)anilino]thieno[3,2-d] pyrimidine hydrochloride

4-Chlorothieno[3,2-d]pyrimidine (0.102 g, 0.60 mmol) and 4-(2-thienylmethoxy)-aniline (prepared according to the published method: WO 96/09294) (0.135 g, 0.66 mmol) were reacted in 2-propanol (5 ml) for 2 hours, according to Procedure A. The product was obtained as a grey-green solid (0.138 g, 61%) with m.p. 181–182° C.; (Found: C, 53.64; H, 3.61; N, 11.04. $C_{17}H_{13}N_3OS_2.HCl.0.25H_2O$ requires: C, 53.68; H, 3.84; N, 11.05%); δH [$^2H_6$]-DMSO 11.28 (1H, br s, NH), 8.75 (1H, s, 2-H), 8.45 (1H, d, J 7, 6 H or 7 H) 7.45–7.68 (4H, m, 6H or 7H, 2'-H, 6'-H, 5"-H), 6.95–7.28 (4H, m, 3'-H, 5'-H, 3"-H, 4"-H), 5.32 (2H, s, $CH_2$); m/z 339 (M⁺).

Example 32

4-(4-Cyclohexylmethoxyanilino)thieno[3,2-d] pyrimidine hydrochloride

4-Chlorothieno[3,2-d]pyrimidine (0.171 g, 1.00 mmol) and 4-cyclohexylmethoxy-aniline (prepared according to the published method: WO 96/09294) (0.205 g, 1.00 mmol) were reacted in 2-propanol (5 ml) for 5 hours, according to Procedure A. The product was obtained as cream prisms (0.255 g, 68%) with m.p. 232–233° C.; (Found: C, 60.65; H, 5.68; N, 11.25. $C_{19}H_{21}N_3OS.HCl$ requires: C, 60.71; H, 5.90; N, 11.23%); δH [$^2H_6$]-DMSO 11.11 (1H, br s, NH), 8.71 (1H, s, 2-H), 8.41 (1H, d, J 7,6 H or 7 H) 7.44–7.58 (3H, m, 6H or 7H, 2'-H, 6'-H), 7.03 (2H, d, J 9, 3'-H, 5'-H), 3.84 (2H, s, $CH_2$), 1.58–1.90 (6H, m) and 0.98–1.33 (5H, m) (cyclohexyl-$H_{11}$); m/z 339 (M⁺).

Example 33

7-Methyl-4-(4-phenoxyanilino)thieno[3,2-d] pyrimidine hydrochloride

4-Chloro-7-methylthieno[3,2-d]pyrimidine (commercially available from Maybridge Chemical Co. Ltd.) (0.185 g, 1.00 mmol) and 4-phenoxyaniline (0.210 g, 1.1 mmol) were reacted in 2-propanol (5 ml) for 2 hours according to Procedure A. The product was obtained as a yellow solid (0.294 g, 80%), m.p. 243–245° C.; (Found: C, 61.46; H, 4.27, N, 11.32. $C_{19}H_{15}N_3OS.HCl$ requires: C, 61.70; H, 4.36; N, 11.36%); δH [$^2H_6$]-DMSO 10.85 (1H, br s, NH), 8.78 (1H, s, 2-H), 8.05 (1H, 2, 6-H), 7.69 (2H, d, J 9, 2'-H, 6'-H), 7.42 (2H, t, J 9, 3"-H, 5"-H), 7.00–7.20 (5H, m, 3'-H, 5'-H, 2"-H, 4"-H, 6"-H), 2.43 (3H, s, 7-$CH_3$); m/z (%) 333 (M⁺).

Example 34

4-(4-Benzyloxy-3-trifluoromethylanilino)-7-methylthieno[3,2-d]pyrimidine hydrochloride 4-Chloro-7-methylthieno[3,2-d]pyrimidine (0.111 g, 0.60 mmol) and 4-benzyloxy-3-trifluoromethylaniline (prepared according to the published method: WO 96/09294) (0.194 g, 0.78 mmol) were reacted in 2-propanol (4.5 ml) for 4 hours according to Procedure A. The product was obtained as a pale pink solid (0.257 g, 95%), m.p. 219–220° C.; (Found: C, 56.30; H, 4.91, N, 8.21. $C_{21}H_{18}F_3N_3OS.HCl.iPrOH$ requires: C, 56.30; H, 4.89; N, 8.21%); δH [$^2H_6$]-DMSO 11.12 (1H, br s, NH), 8.81 (1H, s, 2-H), 8.12 (1H, s, 6-H), 8.02 (1H, d, J 2, 2'-H), 7.97 (1H, dd, J 9,2, 6'-H), 7.29–7.49 (6H, m, 5-H, $PhH_5$), 5.32 (2H, s, $CH_2$), 5.79 (1H, sept, J 6, CHOH of iPrOH), 2.45 (3H, s, 7-$CH_3$), 1.05 (6H, d, J 6, $C(CH_3)_2$ of iPrOH); m/z (%) 415 (M⁺).

Example 35

4-[3-Chloro-4-(2-fluorobenzyloxy)anilino]-5-methylthieno[2,3-d]pyrimidine hydrochloride 4-Chloro-5-methylthieno[2,3-d]pyrimidine (commercially available from Maybridge Chemical Co. Ltd.) (0.092 g, 0.50 mmol) and 3-chloro-4-(2-fluorobenzyloxy)aniline (prepared according to the published method: WO 96/09294) (0.164 g, 0.65 mmol) were reacted in 2-propanol (3.5 ml) for 4 hours, according to Procedure A. The product was obtained as cream plates (0.156 g, 72%) with m.p. 193–196° C.; (Found: C, 55.17; H, 3.77; N, 9.56. $C_{20}H_{15}ClFN_3OS.HCl$ requires: C, 55.05; H, 3.70; N, 9.63%); δH [$^2H_6$]-DMSO 8.39 (1H, s, 2-H), 8.37 (1H, br s, N—H), 7.75 (1H, d, J 4, 2'-H), 7.49–7.59 (2H, m), 7.34–7.44 (1H, m), 7.15–7.32 (4H, m) (6-H, 5'-H, 6'-H, 3"-H, 4"-H, 5"-H, 6"-H), 5.19 (2H, s, $CH_2$), 2.69 (3H, s, 5-$CH_3$); m/z 400 (M+1⁺).

Example 36

4-(4-Cyclohexylmethoxyanilino)-5-methylthieno[2,3-d]pyrimidine hydrochloride 4-Chloro-5-methylthieno[2,3-d]pyrimidine (0.092 g, 0.50 mmol) 4-cyclohexylmethoxyaniline (prepared according to the published method: WO 96/09294) (0.133 g, 0.65 mmol) were reacted in 2-propanol (3.5 ml) for 8 hours according to Procedure A. The product was obtained as a colourless solid (0.120 g, 62%), m.p. 180–183° C.; (Found: C, 60.83; H, 6.10, N, 10.53. $C_{20}H_{23}N_3OS.HCl.0.25H_2O$ requires: C, 60.90; H, 6.22; N, 10.65%); δH [$^2H_6$]-DMSO 8.48 (1H, br s, NH), 8.39 (1H, s, 2-H), 7.50 (2H, d, J 9, 2'-H, 6'-H), 7.31 (1H, s, 6-H), 6.97 (2H, d, J 9, 3'-H, 5'-H), 3.81 (2H, d, J 8, $CH_2$), 2.73 (3H, s, 5-$CH_3$), 1.60–1.88 (6H, m) and 0.98–1.45 (5H, m) (cyclohexyl-$H_{11}$); m/z 354 (M+1⁺).

Example 37

5-Methyl4-(4-phenoxyanilino)thieno[2,3-d] pyrimidine hydrochloride

4-Chloro-5-methylthieno[2,3-d]pyrimidine (0.185 g, 1.00 mmol) and 4-phenoxyaniline (0.210 g, 1.1 mmol) were reacted in 2-propanol (6 ml) for 17 hours according to Procedure A. The product was obtained as a pale grey solid (0.297 g, 80%), m.p. 218–221° C.; (Found: C, 61.61; H, 4.33, N, 11.25. $C_{19}H_{15}N_3OS.HCl$ requires: C, 61.70; H, 4.36; N, 11.36%); δH [$^2H_6$]-DMSO 8.60 (1H, br s, NH), 8.49 (1H, s, 2-H), 7.68 (2H, d, J 9, 2'-H, 6'-H), 7.33–7.48 (3H, m, 6-H, 3"-H, 5"-H), 7.17 (1H, t, J 9, 4"-H), 7.00–7.10 (4H, m, 3'-H, 5'-H, 2"-H, 6"-H), 2.75 (3H, s, 5-$CH_3$); m/z 333 (M⁺).

Example 38

4-(4-Phenoxyanilino)-5-(2-thienyl)thieno[2,3-d] pyrimidine hydrochloride

4-Chloro-5-(2-thienyl)thieno[2,3-d]pyrimidine (commercially available from Maybridge Chemical Co.

Ltd.) (0.126 g, 0.50 mmol) and 4-phenoxyaniline (0.116 g, 0.63 mmol) were reacted in 2-propanol (3 ml) for 6.5 hours according to Procedure A. The product was obtained as an off-white powder (0.150 g, 71%), m.p. 171–172° C. (effervescence); (Found: C, 62.60; H, 3.60, N, 9.85. $C_{22}H_{15}N_3OS_2$.0.67HCl requires: C, 62.06; H, 3.71; N, 9.87%); δH [$^2H_6$]-DMSO 8.58 (1H,s), 7.79–7.85 (2H,m), 7.29–7.56 (7H,m), 6.93–7.13 (5H,m); m/z 401 (M$^+$).

Example 39

4-(4-Benzyloxy-3-chloroanilino)-6-(N,N-dimethylamino)pyrido[3,4-d]pyrimidine hydrochloride Prepared according to Procedure A from 4-chloro-6-(N,N-dimethylamino)pyrido[3,4-d]pyrimidine and 4-benzyloxy-3-chloroaniline (prepared according to the published method: WO96/09294); tlc (dichloromethane:ethanol:aq. ammonia, 100:8:1) Rf 0.48; m/z (M+1)$^+$406.

Example 40

6-(N,N-Dimethylamino)-4-[4-(1-phenyl-1-cyanomethyl)anilino]pyrido[3,4-d]pyrimidine hydrochloride Prepared according to Procedure A from 4-chloro-6-(N,N-dimethylamino)pyrido[3,4-d]pyrimidine and (4-aminophenyl)-phenylacetonitrile (commercially available from Salor); tlc (dichloromethane:ethanol:aq.ammonia, 100:8:1) Rf 0.43; m/z (M+1)$^+$381.

Example 41

6-(N,N-Dimethylamino)-4-[4-(1-phenyl-1,2-dioxoethyl-2-yl)anilino]-pyrido[3,4-d]pyrimidine hydrochloride Prepared according to Procedure A from 4-chloro-6-(N,N-dimethylamino)-pyrido[3,4-d]pyrimidine and 1-(4-aminophenyl)-2-phenylethan-1,2-dione (commercially available from Salor); tlc (dichloromethane:ethanol:ammonia, 100:8:1) Rf 0.44; m/z (M+1)$^+$398.

Example 42

6-(N,N-Dimethylamino)-4-[4-(2-pyridylmethoxy)anilino]-pyrido[3,4-d]pyrimidine hydrochloride 4-(2-Pyridylmethoxy)aniline was prepared from 4-nitrophenol (Aldrich) and 2-picolyl chloride hydrochloride (Aldrich) according to Procedure D. This was reacted with 4-chloro-6-(N,N-dimethylamino)pyrido[3,4-d]pyrimidine according to Procedure A to give the product; tlc (dichloromethane:ethanol:aq.ammonia, 100:8:1) Rf 0.37; m/z (M+1)$^+$373.

Example 43

6-(N,N-Dimethylamino)-4-[4-(2-fluorobenzyloxy)anilino]pyrido[3,4-d]pyrimidine hydrochloride 4-(2-Fluorobenzyloxy)aniline was prepared from 4-nitrophenol (Aldrich) and 2-fluorobenzylbromide (Aldrich) according to Procedure D. This was reacted with 4-chloro-6-(N,N-dimethylamino)pyrido[3,4-d]pyrimidine according to Procedure A to give the product; tlc (dichloromethane:ethanol:aq.ammonia, 100:8:1) Rf 0.48; m/z (M+1)$^+$390.

Example 44

6-(N,N-Dimethylamino)-4-[4-(3-fluorobenzyloxy)anilino]pyrido[3,4-d]pyrimidine hydrochloride 4-(3-Fluorobenzyloxy)aniline was prepared from 4-nitrophenol (Aldrich) and 3-fluorobenzylbromide (Aldrich) according to Procedure D. This was reacted with 4-chloro-6-(N,N-dimethylamino)pyrido[3,4-d]pyrimidine according to Procedure A to give the product; tlc (dichloromethane:ethanol:aq.ammonia, 100:8:1) Rf 0.48; m/z (M+1 )$^+$390.

Examples 45 to 49

The following compounds are prepared by analogous techniques using the appropriate starting materials:

4-(4-Phenylsulphonylanilino)-6-(1-methylimidazol-2-yl)-pyrido[3,4-d]pyrimidine;
4-(4-Benzyloxyanilino)-7-dimethylamino-pyrido[4,3-d]pyrimidine;
4-(4-Benzyloxyanilino)-6-(2-imidazolyl)pyrido[3,4-d]pyrimidine;
4-(4-Benzyloxyanilino)-6-(5-carboxyfuran-2-yl)-pyrido[3,4-d]pyrimidine.

Biological Data

Compounds of the present invention were tested for protein tyrosine kinase inhibitory activity in a substrate phosphorylation assay and a cell proliferation assay.

The substrate phosphorylation assay uses a baculovirus expressed, recombinant construct of the intracellular domain of c-erbB-2 that is constitutively active. The method measures the ability of the isolated enzyme to catalyse the transfer of $^{33}$P-labelled γ-phosphate from ATP onto tyrosine residues in a synthetic peptide. The enzyme is incubated for 1 hour, at room temperature, with 100 μM ATP, 10 mM MnCl$_2$, 1 mg/ml PolyGluAlaTyr (6:3:1) and test compound (diluted from a 5 mM stock in DMSO, final DMSO concentration is 2%) in 40 mM HEPES buffer, pH 7.4. The reaction is stopped by the addition of EDTA (final concentration 0.1M) and the peptide is then precipitated onto ion exchange filter paper and the incorporated radioactivity determined. The results are shown in the first column of Table 1 below as the IC$_{50}$ values in nM.

The cell proliferation assay uses an immortalised human breast epithelial cell line (HB4a) which has been transformed by over-expression of c-erbB-2. Growth of these cells in low serum is dependent upon the c-erbB-2 tyrosine kinase activity. The specificity of the effect of the test compounds on tyrosine kinase dependent growth over general toxicity is assessed by comparison to an HB4a cell line which has been transfected with ras. Cells are plated at 3000/well in 96-well plates in 0.1 ml medium and allowed to attach overnight. test compound is added in 0.1 ml medium, with a final concentration of 0.5% DMSO, and the plates incubated for 4 days at 37° C. The cells are then examined microscopically for evidence of morphological detransformation and cell mass is estimated by staining with methylene blue and measuring the absorbance at 620 nm. The results are shown in the second and third columns of Table 1 below as the IC$_{50}$ values in nM.

TABLE 1

| Compound of Example | erbB-2 Substrate Phosphorylation | HB4a erbB-2 Cell Proliferation | HB4a ras Cell Proliferation |
|---|---|---|---|
| 1 | 58 | 2700 | 17000 |
| 2 | 26 | 690 | 3700 |
| 3 | 115 | 11000 | 44000 |
| 4 | 124 | 2500 | 11000 |
| 5 | 14 | 500 | 11000 |
| 7 | 1.3 | 300 | >50000 |
| 8 | 20 | 590 | 7500 |
| 11 | 920 | 10000 | 37000 |
| 12 | 24 | 1600 | 31000 |
| 14 | 900 | 15000 | 50000 |
| 15 | 30 | 570 | 32000 |
| 16 | 50 | 2400 | 6600 |
| 17 | 200 | 4400 | 10000 |
| 18 | 5 | 150 | 28000 |
| 20 | 10 | 2400 | 46000 |
| 23 | 300 | 2000 | 5000 |
| 24 | 50 | 10000 | 18000 |
| 25 | 150 | 500 | 3000 |
| 26 | 230 | 2500 | 30000 |
| 28 | 200 | 3000 | 13000 |
| 29 | 110 | 5000 | 20000 |
| 30 | 860 | 6000 | 15000 |
| 35 | 99 | 8000 | 25000 |
| 36 | 500 | 10000 | 10000 |
| 37 | 650 | 17000 | 25000 |
| 38 | 490 | 20000 | 20000 |

What is claimed is:

1. A compound of formula (A):

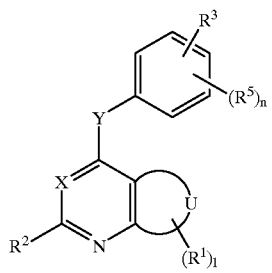

(A)

or a pharmaceutically acceptable salt thereof,
wherein X is N;
Y is a group $W(CH_2)$, $(CH_2)W$, or W, in which W is O, $S(O)_m$, or $NR^a$ wherein m is 0,1, or 2 and $R^a$ is hydrogen or a $C_{1-8}$ alkyl group;

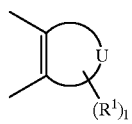 is selected from the group consisting of:

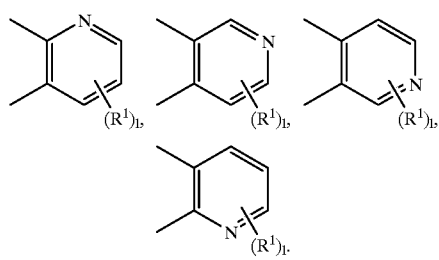

each $R^1$ independently represents a 5- or 6-membered heterocyclic ring containing 1 to 4 heteroatoms selected from N, O or $S(O)_m$, wherein m is as defined above, with the proviso that the ring does not contain two adjacent O or $S(O)_m$ atoms, optionally substituted by one or more groups independently selected from hydroxy, halogen, trifluoromethyl, trifluoromethoxy, nitro, amino, cyano, $C_{1-4}$ alkyl, $C_{1-4}$ alkoxy, $C_{1-4}$ alkylthio, $C_{1-4}$ alkyl carbonyl, formyl, carboxy, $C_{1-4}$ alkoxy carbonyl, carboxamide, $C_{1-4}$ alkylamino carbonyl, ($C_{1-4}$ alkyl)amino, di-($C_{1-4}$ alkyl) amino; or each $R^1$ is independently selected from the group consisting of amino, hydrogen, halogen, hydroxy, nitro, formyl, carboxy, trifluoromethyl, trifluoromethoxy, carbamoyl, ureido, $C_{1-8}$ alkyl, $C_{1-8}$ alkoxy, $C_{3-8}$ cycloalkoxyl, $C_{4-8}$ alkylcycloalkoxy, $C_{1-8}$ alkoxycarbonyl, N-$C_{1-4}$ alkylcarbamoyl, N,N-di-($C_{1-4}$ alkyl)carbamoyl, hydroxyamino, $C_{1-4}$ alkoxyamino, $C_{2-4}$ alkanoyloxyamino, $C_{1-4}$ alkylamino, di($C_{1-4}$ alkyl) amino, pyrrolidin-1-yl, piperidino, morpholino, thiomorpholino, thiomorpholino-1,1-dioxide, piperazin-1-yl, 4-$C_{1-4}$ alkylpiperazin-1-yl, $C_{1-8}$ alkylthio, arylthio, $C_{1-4}$ alkylsulphinyl, arylsulphinyl, $C_{1-4}$ alkylsulphonyl, arylsulphonyl, halogeno-$C_{1-4}$ alkyl, hydroxy-$C_{1-4}$ alkyl, $C_{2-4}$ alkanoyloxy-$C_{1-4}$ alkyl, $C_{1-4}$ alkoxy-$C_{1-4}$ alkyl, carboxy-$C_{1-4}$ alkyl, $C_{1-4}$ alkoxycarbonyl-$C_{1-4}$-alkyl, amino-$C_{1-4}$ alkyl, $C_{1-4}$ alkylamino-$C_{1-4}$ alkyl, di-($C_{1-4}$ alkyl)amino-$C_{1-4}$ alkyl, (di-$C_{1-4}$ alkyl)amino-$C_{1-4}$ alkylene-($C_{1-4}$ alkyl)amino, $C_{1-4}$alkylamino-$C_{1-4}$alkylene-($C_{1-4}$alkyl)amino, hydroxy-$C_{1-4}$alkylene-($C_{1-4}$alkyl)amino, piperidino-$C_{1-4}$alkyl, morpholino-$C_{1-4}$ alkyl, thiomorpholino-$C_{1-4}$ alkyl, thiomorpholino-1,1-dioxide-$C_{1-4}$ alkyl, piperazin-1-yl-$C_{1-4}$ alkyl, $C_{1-4}$ alkylthio-$C_{1-4}$ alkyl, phenoxy-$C_{1-4}$ alkyl, anilino-$C_{1-4}$ alkyl, phenylthio-$C_{1-4}$ alkyl, cyano-$C_{1-4}$ alkyl, halogeno-$C_{2-4}$ alkoxy, hydroxy-$C_{2-4}$ alkoxy, $C_{2-4}$ alkanoyloxy-$C_{2-4}$ alkoxy, $C_{1-4}$ alkoxy-$C_{2-4}$ alkoxy, carbamoyl-$C_{1-4}$ alkoxy, amino-$C_{2-4}$ alkoxy, $C_{1-4}$ alkylamino-$C_{2-4}$ alkoxy, di-($C_{1-4}$ alkyl)amino-$C_{2-4}$ alkoxy, phenyl-$C_{1-4}$ alkoxy, phenoxy-$C_{2-4}$ alkoxy, anilino-$C_{2-4}$ alkoxy, phenylthio-$C_{2-4}$ alkoxy, piperidino-$C_{2-4}$ alkoxy, morpholino-$C_{2-4}$ alkoxy, thiomorpholino-$C_{2-4}$ alkoxy, thiomorpholino-1,1-dioxide-$C_{2-4}$ alkoxy, piperazin-1-yl-$C_{2-4}$ alkoxy, halogeno-$C_{2-4}$ alkylamino, hydroxy-$C_{2-4}$ alkylamino, $C_{2-4}$ alkanoyloxy-$C_{2-4}$ alkylamino, $C_{1-4}$ alkoxy-$C_{2-4}$ alkylamino, phenyl-$C_{1-4}$ alkylamino, phenoxy-$C_{2-4}$ alkylamino, anilino-$C_{2-4}$ alkylamino, phenylthio-$C_{2-4}$ alkylamino, $C_{2-4}$ alkanoylamino, $C_{1-4}$ alkoxycarbonylamino, $C_{1-4}$ alkylsulphonylamino, benzamido, benzenesulphonamido, 3-phenylureido, 2-oxopyrrolidin-1-yl, 2,5-dioxopyrrolidin-1-yl, halogeno-$C_{2-4}$ alkanoylamino, hydroxy-$C_{2-4}$ alkanoylamino, $C_{1-4}$ alkoxy-$C_{2-4}$ alkanoylamino, and carboxy-$C_{2-4}$ alkanoylamino, and wherein said benzamido or benzenesulphonamido substituent or any anilino, phenoxy or phenyl group on a $R^1$ substituent may optionally bear one or two halogeno, $C_{1-4}$ alkyl or $C_{1-4}$ alkoxy substituents;

and 1 is 0 to 3;

or when 1 is 2 or 3, two adjacent $R^1$ groups together form an optionally substituted methylenedioxy or ethylenedioxy group;

R² is selected from the group consisting of; hydrogen, halogen, trifluoromethyl, $C_{1-4}$ alkyl and $C_{1-4}$ alkoxy;

R³ is selected from the group consisting of benzyl, phenyl, pyridyl, pyridylmethyl, pyridyloxy, pyridylmethoxy, thienylmethoxy, dioxolanylmethoxy, cyclohexylmethoxy, phenoxy, phenylthio, benzyloxy, halo-, dihalo- and trihalobenzyloxy, $C_{1-4}$ alkoxybenzyloxy, phenyloxalyl or phenylsulphonyl;

each R⁵ is independently selected from the group consisting of; hydrogen, hydroxy, halogen, $C_{1-4}$ alkyl, $C_{1-4}$ alkoxy, $C_{1-4}$ alkylamino, di-[$C_{1-4}$ alkyl]amino, $C_{1-4}$ alkylthio, $C_{1-4}$ alkylsulphinyl, $C_{1-4}$ alkylsulphonyl, $C_{1-4}$ alkylcarbonyl, $C_{1-4}$ alkylcarbamoyl, di[$C_{1-4}$ alkyl]carbamoyl, carbamyl, $C_{1-4}$ alkoxycarbonyl, cyano, nitro and trifluoromethyl, and n is 1,2 or 3.

2. A compound as claimed in claim 1, wherein X is N and Y is NR$^a$, R$^a$ representing hydrogen or methyl.

3. A compound as claimed in claim 1, wherein R¹ is selected from the group consisting of phenyl, furan, thiophene, pyrrole, oxazole, isoxazole, thiazole, isothiazole, imidazole, pyrazole and piperazine or a hydrogenated derivative of any of the aforementioned and is optionally substituted by one or more groups selected from hydroxy, halogen, trifluoromethyl, trifluoromethoxy, nitro, amino, cyano, $C_{1-4}$ alkyl, $C_{1-4}$ alkoxy, $C_{1-4}$ alkylcarbonyl, $C_{1-4}$ alkoxycarbonyl, formyl or carboxy;

or R¹ is independently selected from the group consisting of amino, hydrogen, halogen, hydroxy, nitro, $C_{1-8}$ alkyl, $C_{1-8}$ alkoxy, benzyloxy, morpholino, thiomorpholino, thiomorpholino-1,1-dioxide, pyrrolidino, piperidino, $C_{1-8}$ alkylthio, $C_{1-8}$ alkylsulphinyl, $C_{1-8}$ alkylsulphonyl, $C_{1-4}$ alkylamino, $C_{1-4}$ dialkylamino, [di-$C_{1-4}$ alkyl]amino-$C_{1-4}$ alkylene-($C_{1-4}$ alkyl)amino, $C_{1-4}$alkylamino-$C_{1-4}$alkylene-($C_{1-4}$alkyl)amino or hydroxy-$C_{1-4}$alkylene-($C_{1-4}$alkyl)amino.

4. A compound as claimed in claim 1, wherein R¹ is selected from the group consisting of phenyl, furan, pyrazole, imidazole and piperazine, optionally substituted by one or more groups selected from $C_{1-4}$ alkyl, formyl, carboxy or $C_{1-4}$ alkoxycarbonyl; or R¹ is independently selected from the group consisting of hydrogen, halogen, $C_{1-4}$ alkyl, benzyloxy, thiomorpholino, thiomorpholino-1,1-dioxide, $C_{1-4}$ alkylamino, $C_{1-4}$ dialkylamino, [di-$C_{1-4}$ alkyl]amino-$C_{1-4}$ alkylene-($C_{1-4}$ alkyl)amino, $C_{1-4}$alkylamino-$C_{1-4}$ alkylene-($C_{1-4}$ alkyl)amino or hydroxy-$C_{1-4}$alkylene-($C_{1-4}$alkyl)amino.

5. A compound as claimed in claim 1, wherein R² is hydrogen, $C_{1-4}$ alkyl, $C_{1-4}$ alkoxy or halogen.

6. A compound as claimed in claim 1, wherein R⁵ is hydrogen, hydroxy, halogen, $C_{1-4}$ alkyl, $C_{1-4}$ alkoxy, di-[$C_{1-4}$ alkyl]amino, nitro or trifluoromethyl.

7. A compound as claimed in claim 1 selected from the group consisting of:
  4-(4-Benzyloxyanilino)-6-chloroprido[3,4-d]pyrimidine;
  4-(4-Benzyloxyanilino)-6-(N-methylimidazol-5-yl)pyrido[3,4-d]pyrimidine;
  4(4-Benzyloxy-3-chloroanilino)-6-(N,N-dimethylamino)pyrido[3,4-d]pyrimidine;
  6-(N,N-Dimethylamino)-4-[4-(1-phenyl-1,2-dioxoethyl-2-yl)anilino]-pyrido[3,4-d]pyrimidine;
  6-(N,N-Dimethylamino)-4-[4-(pyridyl-2-methoxy)anilino]-pyrido[3,4-d]pyrimidine;
  6-(N,N-Dimethylamino)-4-[4-(2-fluorobenzyloxy)anilino]pyrido[3,4-d]pyrimidine;
  6-(N,N-Dimethylamino)-4-[4-(3-fluorobenzyloxy)anilino]pyrido[3,4-d]pyrimidine;
or pharmaceutically acceptable salts thereof.

8. A compound as claimed in claim 1 selected from the group consisting of:
  4-(4-Benzyloxyanilino)-6-(N-methylimidazol-5-yl)pyrido[3,4-d]pyrimidine;
  4-(4-Benzyloxyanilino)-6-(N,N-dimethylamino)pyrido[3,4-d]pyrimidine;
  6-(N,N-Dimethylamino)-4-[4-(1,3-dioxolan-2-yl)methoxyanilino]pyrido[3,4-d]pyrimidine;
or pharmaceutically acceptable salts thereof.

9. A pharmaceutical formulation comprising one or more compounds of formula (A), as claimed in claim 1, or pharmaceutically acceptable salt(s) thereof, together with one or more pharmaceutically acceptable carriers, diluents or excipients.

10. A pharmaceutical formulation as claimed in claim 9 in unit dosage form and containing a compound of formula (A) or a pharmaceutically acceptable salt thereof in an amount from 70 to 700 mg.

11. A process for the preparation of a compound of formula (A), as claimed in claim 1, comprising the reaction of a compound of formula (B):

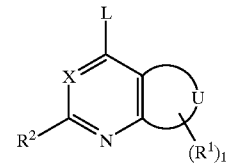

(B)

with a compound of the formula C:

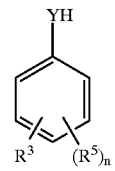

(C)

wherein L is a leaving group and X, Y, I, n and R¹ to R⁵ are as defined in claim 1.

12. A process as claimed in claim 11 wherein the process also includes the step of converting one compound of formula (B) into another compound of formula (B) prior to the reaction with the compound of formula (C).

13. A process as claimed in claim 11 wherein the process also includes the step of converting one compound of formula (C) into another compound of formula (C) prior to the reaction with the compound of formula (B).

14. A process as claimed in claim 1, the process also including the step of converting one compound of formula (A) into another compound of formula (A).

15. A method of treatment of a human or animal subject suffering from a disorder mediated by aberrant tyrosine kinase activity which comprises administering to the human or animal subject an effective amount of a compound of formula (A) as claimed in claim 1 or a pharmaceutically acceptable salt thereof.

* * * * *